US012558502B2

(12) United States Patent (10) Patent No.: US 12,558,502 B2
White et al. (45) Date of Patent: Feb. 24, 2026

(54) METHODS AND APPARATUS FOR HIGH GAS FLOW

(71) Applicant: Fisher & Paykel Healthcare Limited, Auckland (NZ)

(72) Inventors: Craig Karl White, Auckland (NZ); Alicia Jerram Hunter Evans, Auckland (NZ); Matthew Jon Payton, Auckland (NZ); Geraldine Frances Keogh, Auckland (NZ); Nicholas Simon David Connolly, Auckland (NZ); Anil Patel, Auckland (NZ); Seyed Ahmad Reza Nouraei, London (GB)

(73) Assignee: Fisher & Paykel Healthcare Limited, Auckland (NZ)

( * ) Notice: Subject to any disclaimer, the term of this patent is extended or adjusted under 35 U.S.C. 154(b) by 36 days.

(21) Appl. No.: 18/629,590

(22) Filed: Apr. 8, 2024

(65) Prior Publication Data
US 2024/0390617 A1     Nov. 28, 2024

Related U.S. Application Data

(63) Continuation of application No. 17/857,862, filed on Jul. 5, 2022, now Pat. No. 11,980,713, which is a
(Continued)

(51) Int. Cl.
*A61M 16/00* (2006.01)
*A61M 16/01* (2006.01)
(Continued)

(52) U.S. Cl.
CPC .... *A61M 16/0096* (2013.01); *A61M 16/0051* (2013.01); *A61M 16/01* (2013.01);
(Continued)

(58) Field of Classification Search
CPC .......... A61M 16/0096; A61M 16/0051; A61M 16/01; A61M 16/024; A61M 16/0672;
(Continued)

(56) References Cited

U.S. PATENT DOCUMENTS 3,683,700 A     8/1972  Wilfong
5,349,946 A     9/1994  McComb
(Continued)

FOREIGN PATENT DOCUMENTS

WO     WO 2011/073839     6/2011
WO     WO 2013/148754     10/2013
(Continued)

OTHER PUBLICATIONS

Badiger, S., A. Fearnley, and I. Ahmad. "High flow nasal cannula as an oxygen delivery device during awake fibreoptic intubation." Anaesthesia 69 (2014): 12.
(Continued)

*Primary Examiner* — Elliot S Ruddie
(74) *Attorney, Agent, or Firm* — Knobbe Martens Olson & Bear LLP

(57)     ABSTRACT
Several methods of supporting respiratory function of a patient before, during and/or after a medical procedure are disclosed. In certain arrangements, supporting respiratory function while a patient is under general anaesthesia can include providing a high gas flow a high gas flow that is greater than 15 L/min while the patient is under general anaesthesia. In certain arrangements, a method of providing ventilation while a patient is under general anaesthesia involves providing only a gas flow delivered through a nasal interface that is greater than 15 L/min while the patient is under general anaesthesia.

49 Claims, 13 Drawing Sheets

Related U.S. Application Data continuation of application No. 15/562,880, filed as application No. PCT/IB2016/051816 on Mar. 31, 2016, now Pat. No. 11,419,997.

(60) Provisional application No. 62/232,231, filed on Sep. 24, 2015, provisional application No. 62/140,727, filed on Mar. 31, 2015.

(51) Int. Cl.

| | |
|---|---|
| *A61M 16/04* | (2006.01) |
| *A61M 16/06* | (2006.01) |
| *A61M 16/10* | (2006.01) |
| *A61M 16/12* | (2006.01) |
| *A61M 16/16* | (2006.01) |

(52) U.S. Cl.
CPC ...... *A61M 16/024* (2017.08); *A61M 16/0672* (2014.02); *A61M 16/1005* (2014.02); *A61M 16/12* (2013.01); *A61M 16/16* (2013.01); *A61M 2016/0027* (2013.01); *A61M 2016/0039* (2013.01); *A61M 16/04* (2013.01); *A61M 16/0461* (2013.01); *A61M 16/06* (2013.01); *A61M 2016/1025* (2013.01); *A61M 16/161* (2014.02); *A61M 2202/0208* (2013.01); *A61M 2205/3368* (2013.01); *A61M 2205/502* (2013.01); *A61M 2230/205* (2013.01); *A61M 2230/432* (2013.01)

(58) Field of Classification Search
CPC .. A61M 16/1005; A61M 16/12; A61M 16/16; A61M 16/04; A61M 16/0461; A61M 16/06; A61M 16/161; A61M 2016/0027; A61M 2016/0039; A61M 2016/1025; A61M 2202/0208; A61M 2205/3368; A61M 2205/502; A61M 2230/205; A61M 2230/432

See application file for complete search history.

(56) References Cited

U.S. PATENT DOCUMENTS

| | | | |
|---|---|---|---|
| 5,509,406 A | 4/1996 | Kock et al. | |
| 5,558,083 A | 9/1996 | Bathe et al. | |
| 5,957,129 A * | 9/1999 | Tham .................. | A61M 16/104 |
| | | | 128/204.22 |
| 6,186,142 B1 | 2/2001 | Schmidt et al. | |
| 6,371,114 B1 | 4/2002 | Schmidt et al. | |
| 6,523,537 B1 | 2/2003 | Mas Marfany | |
| 6,622,726 B1 | 9/2003 | Du | |
| 6,694,969 B1 | 2/2004 | Heinonen et al. | |
| 7,493,902 B2 | 2/2009 | White et al. | |
| 7,861,717 B1 | 1/2011 | Krebs | |
| 10,159,815 B2 | 12/2018 | Orr | |
| 2002/0117174 A1 | 8/2002 | Colas | |
| 2006/0042631 A1 | 3/2006 | Martin et al. | |
| 2006/0042638 A1 * | 3/2006 | Niklewski ......... | A61M 16/0858 |
| | | | 128/207.18 |
| 2006/0174889 A1 | 8/2006 | Noble | |
| 2006/0196505 A1 | 9/2006 | Izuchukwu | |
| 2007/0175473 A1 | 8/2007 | Lewis et al. | |

| | | | |
|---|---|---|---|
| 2008/0051674 A1 * | 2/2008 | Davenport .......... | A61M 16/161 |
| | | | 128/207.18 |
| 2010/0022849 A1 | 1/2010 | Franz | |
| 2010/0252039 A1 | 10/2010 | Cipollone | |
| 2011/0066061 A1 | 3/2011 | Colman et al. | |
| 2012/0017904 A1 | 1/2012 | Ratto | |
| 2013/0104888 A1 | 5/2013 | Landis et al. | |
| 2014/0275901 A1 | 9/2014 | Flanagan et al. | |
| 2015/0020801 A1 | 1/2015 | Frame et al. | |
| 2015/0119742 A1 | 4/2015 | Tse | |
| 2016/0082220 A1 | 3/2016 | Barker | |
| 2016/0193438 A1 | 7/2016 | White | |
| 2018/0126110 A1 | 5/2018 | Payton | |
| 2018/0280641 A1 | 10/2018 | White et al. | |
| 2019/0298949 A1 | 10/2019 | Nightingale | |

FOREIGN PATENT DOCUMENTS

| | | |
|---|---|---|
| WO | WO 2013/163685 | 11/2013 |
| WO | WO 2015/033288 | 3/2015 |
| WO | WO 2016/157102 | 10/2016 |

OTHER PUBLICATIONS

Davison et al. "The Effects of Anaesthesia on Respiratory Function", Nov. 15, 2010 (Year: 2010).

European Supplemental Search Report for Application No. EP 16 77 1498, Oct. 16, 2018.

European Supplementary Search Report, Application No. PCT/NZ2016/050020, dated Mar. 9, 2018, in 9 pages.

Examination Report for Australian Patent Application No. 2015230787, dated Feb. 24, 2021 in 3 pages.

Farkas "Preoxygenation & apneic oxygenation using a nasal cannula", Jul. 2, 2014, PULMCrit, https://emcrit.org/pulmcrit/preoxygenation-apneic-oxygenation-using-a-nasal-cannula/.

Heinrich et al. "Benefits of Heated and Humidified High Flow Nasal Oxygen for Preoxygenation in Morbidly Obese Patients Undergoing Bariatric Surgery: A Randomized Controlled Study." J Obes Bariatrics (Dec. 2014) vol. 1, Issue 1.

International Search Report and Written Opinion in PCT/IB2016/051816 dated Jun. 29, 2016 in 13 pages.

International Search Report, Application No. PCT/NZ2016/050020, dated May 6, 2016, in 3 pages.

Lucangelo et al. "High-Flow Nasal Interface Improves Oxygenation in Patients Undergoing Bronchoscopy" Critical Care Research and Practice; vol. 2012, Article ID 506382, 6 pages, (Mar. 23, 2012).

Montanes et al. "Use of High-Flow Nasal Cannula Oxygen Therapy to Prevent Desaturation During Tracheal Intubation of Intensive Care Patients With Mild-to-Moderate Hypoxemia" Critcal Care Medicine (Mar. 2015) 574-83.

Patel, A., and S. A. R. Nouraei. "Transnasal Humidified Rapid-Insufflation Ventilatory Exchange (THRIVE): A physiological method of increasing apnoea time in patients with difficult airways." Anaesthesia (2014) pp. 1-7.

Reuben, "The High Flow Nasal Cannula in the Emergency Department." Emergency Medicine Updates dated Mar. 1, 2012 in 3 pages.

Shelly, M.P. "A review of the mechanisms and methods of humidification of inspired gases", 1988, vol. 14, pp. 1-9. (Year: 1988).

Weingart et al., "Preoxygenation and Prevention of Desaturation During Emergency Airway Management," Annals of Emergency Medicine, Mar. 2012, vol. 59, Issue 3, pp. 165-175.

* cited by examiner

*100*

400

METHODS AND APPARATUS FOR HIGH GAS FLOW

This application claims the benefit as a nonprovisional of U.S. Prov. App. No. 62/140,727 filed on Mar. 31, 2015 and U.S. Prov. App. No. 62/232,231 filed on Sep. 24, 2015, both of which are hereby incorporated by reference in their entireties for all purposes.

FIELD

The present disclosure relates to methods and apparatus for promoting gas exchange (such as oxygenation and/or $CO_2$ removal) to provide, in one application, respiratory support for a patient, in relation to anaesthesia or more generally medical procedures where respiratory function might be compromised.

BACKGROUND

Patients can lose respiratory function during anaesthesia, or more generally during certain medical procedures, respiratory function can diminish or stop.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

SUMMARY

It is therefore an object of one or more of the disclosed embodiments to address the problem of diminished respiratory function or the risk of diminished respiratory function in a patient in relation to medical procedures (including anaesthesia and/or general anaesthesia and/or general anaesthesia wherein the patient is unconscious) and/or to at least provide the public with a useful choice.

In this description, the term "medical procedure" can (as context requires) refer to periods during the medical procedure itself, and/or or the periods before and/or after the medical procedure in which there is a diminished or the risk of diminished respiratory function in a patient. In one embodiment, the medical procedure involves anaesthesia and in certain embodiments general anaesthesia and in certain embodiments general anaesthesia wherein the patient is unconscious. The medical procedure in certain embodiments can also include local anaesthesia.

A continuous supply of oxygen and and/or removal of CO2 is essential to sustain healthy respiratory function during medical procedures (such as during anaesthesia) where respiratory function might be compromised (e.g. diminishes or stops). When e.g. the supply of oxygen and/or removal of CO2 is compromised, hypoxia and/or hypercapnia can occur. During medical procedures such as anaesthesia, the patient can be monitored to ensure this does not happen. If oxygen supply and/or CO2 removal is compromised the clinician stops the medical procedure and facilitates oxygen supply and/or CO2 removal. This can be achieved for example by manually ventilating the patient through an anaesthesia bag and mask.

For example, general anaesthesia is the state produced when a patient receives medications for amnesia, analgesia, muscle paralysis, and sedation. An anesthetized patient can be thought of as being in a controlled, reversible state of unconsciousness. Anaesthesia enables a patient to tolerate surgical procedures that would otherwise inflict unbearable pain, potentiate extreme physiologic exacerbations, and result in unpleasant memories. General anaesthesia can include situations where the patient is conscious (such as under sedation) or where the patient is unconscious.

The combination of anesthetic agents used for general anaesthesia often leaves a patient with the following clinical constellation:

Unarousable even secondary to painful stimuli

Unable to remember what happened (amnesia)

Unable to maintain adequate airway protection and/or spontaneous ventilation as a result of muscle paralysis Cardiovascular changes occur secondary to the stimulant/depressant effects of anaesthetic agents.

Due to the diminished respiratory function, patient breathing needs to be assisted. In order to allow surgery on a patient, it is usually necessary to protect the airway of the anaesthetised patient with a prosthetic airway device such as a laryngeal mask airway or endotracheal tube (ET Tube). Many general anaesthesia patients require placement of an endotracheal tube. Indications for endotracheal intubation include the following:

Potential for airway contamination (e.g. due to full stomach, gastroesophageal [GE] reflux, gastrointestinal [GI] or pharyngeal bleeding)

Surgical need for muscle relaxation

Surgery of the mouth or face

Prolonged surgical procedure

The process of inserting an ET Tube into the trachea is called intubation. Intubation involves visualising the larynx and vocal chords, directly with a laryngoscope or via a flexible fibreoptic or video scope. The ET tube is then inserted through the mouth or nose and passed between the vocal chords into the trachea. The balloon on the end of the ET Tube sits in the trachea below the vocal chords and is inflated to seal in the trachea, and thus a secure and definitive airway is established. In certain applications, the ET Tube can be used to deliver local anaesthesia.

Muscle relaxants cause paralysis and during intubation the patient is not breathing due to this paralysis. It is normal practice to have apnoea (patient not breathing) during the intubation and no respiratory support as most respiratory interfaces such as masks are completely in the way of the anaesthesiologist and their laryngoscope or flexible scope. Once a secure and definitive airway is established the anaesthesiologist can provide ventilation. Apnoea can occur due to, for example, respiratory depression from anaesthesia (or a variety of other causes), such that the patient stops breathing.

Most patients are in this state of apnoea for less than a minute, and while their oxygen levels may begin to drop, they are intubated before their oxygen levels drop to dangerous levels.

The period of time that an anesthesiologist has to secure a definitive airway after the patient stops breathing is referred to as the "apnoeic window." If the airway cannot be established during the apnoeic window, the patient may be harmed and/or the medical procedure may need to be terminated. The standard procedure for increasing the apnoeic window involves pre-oxygenation ventilation through the use of facemasks with 100% oxygen. The goal of the pre-oxygenation is to remove nitrogen from the lungs and establish an oxygen reservoir in the alveoli. While such procedures have been useful, there is a need to improve procedures and apparatuses for increasing the apnoeic window and/or address the problem of diminished respiratory function during a medical procedure. For example, many patients have difficulty using facemasks which can be obtrusive and can inhibit the patient's ability to communicate with the medical staff. In addition, pre-oxygenation with a bag or face mask may not provide consistent positive end-expiratory pressure (PEEP) (i.e., above atmospheric pressure at the end of expiration.) If the facemask needs to be removed, then the patient can rapidly lose oxygenation by breathing room air. In addition, removing the face mask to intubate can result in a loss of pressure and lung recruitment. At the onset of anaesthesia, the patient can lose airway patency, which can lead to airway obstruction and can prevent effective oxygenation. This can be particularly likely for certain groups of patients (e.g. obese patients that have poor muscle tone in their airway and may be predisposed to obstructive sleep apnoea). Accordingly pre-oxygenation by traditional methods can be extremely difficult, take a long time, is technique dependent, and may not be achieved adequately for a safe intubation attempt.

During apnoea, gas exchange is still occurring. The heart is still beating and the blood still circulating. However as there is no breathing, the gas exchange is limited by diffusion of the respiratory gases into and out of the alveolar. The average adult uses about 2-4 ml/min/kg of oxygen, but may be more or less based on their metabolism. The blood is able to take up oxygen at this rate provided enough oxygen is available in the alveolar. Conversely, $CO_2$ is diffused from the blood to the alveolar space but at a slower rate of about 0.1-0.2 ml/min/kg due to the blood's ability to buffer the gas. This mismatch in oxygen and $CO_2$ mass diffusion across the alveolar membrane causes a slight sub-atmospheric pressure in the alveolar space and results in a net movement of gas from the atmosphere and into the non-moving lungs (termed apnoeic oxygenation). The transport of oxygen however does not occur at a sufficient rate, and it is likely the patient's oxygen levels will become critically low over a period of 1 to 5 minutes.

In addition, due to the unfavourable density ratio between carbon dioxide and oxygen ($CO_2$ is approximately 1.5 times heavier) and its affinity and solubility in the blood ($CO_2$ is approximately 25 times more soluble than oxygen) $CO_2$ may occupy a significant volume in the alveolar space and its clearance to the atmosphere occurs at a very slow rate. The body can buffer $CO_2$ and store considerable quantities before it eventually rises high enough to cause $CO_2$ toxicity. However, $CO_2$ can displace oxygen in the alveoli so insufficient removal of $CO_2$ can not only lead to $CO_2$ toxicity but also inhibit oxygenation.

Patients with high metabolic rates or low functional residual capacity in the lungs (FRC) desaturate more quickly during an apnoeic period. Examples of these patient groups include: Pregnant patients as they have both a low lung volume (low FRC) due to the baby squashing the mother's lungs and a high metabolic rate; Obese patients as they have a large weight of fat on the chest and abdomen thus reducing FRC; and Paediatric patients who have relatively high metabolism and unfavourable physiology for maintaining saturation levels during an apnoeic period. The safe apnoeic period for these patients may last less than 30 seconds and requires a fast and efficient intubation or the anaesthesiologist can be immediately under immense stress.

Anaesthesia can increase lung compliance and reduce muscle tone which reduces the patient's FRC. Patients are also often positioned supine which can further reduce FRC. A reduced FRC reduces ventilation and therefore also the ability to oxygenate.

Atelectasis occurs in up to 90% of anaesthetic cases and can be caused by compression, absorption and/or loss of surfactant. There is also risk of post-extubation atelectasis. The amount of atelectasis and airway closure may explain up to 75% of the deterioration in gas exchange seen during general anaesthesia.

Some patients are very difficult to intubate and anaesthesiologists try to identify this through patient examinations prior to the surgery. Some common causes of patients being difficult to intubate include how far they can open their mouth, how high they can lift their chin, obese patients, or other more difficult to identify problems including airway tumours or cysts, polyps on the vocal chords, a narrow or swollen larynx.

The larynx can also go into spasm, which is called laryngospasm and is where the vocal chords and glottis spasm and shut the airway. This can happen during the intubation process, and may be initiated due to stimulus from a scope or an airway device. The laryngospasm can cause complete airway blockage or partial airway blockage which makes it impossible to intubate the patient while it is ongoing.

An unexpectedly difficult to intubate patient is at risk of significant morbidity and mortality, making the patient high risk and can put the anaesthesiologist under immense stress. In certain situations, if the patient can be non-invasively ventilated the anaesthesiologist abandons the intubation attempt and mask ventilates the patient until their oxygen levels are adequate again. In certain situations, a second intubation attempt can then be made and if the anaesthesiologist still cannot secure the airway before the patient's oxygen levels drop too far and the surgery is not an emergency, then usually no more attempts are made, or perhaps one more attempt is made depending upon the situation, and then the patient's anaesthesia is reversed, and the surgery may be abandoned/postponed. Rescheduling the surgery again for another day can be a large expense.

If the patient cannot be ventilated and cannot be intubated the situation is even more serious, for example this situation may be caused by prolonged laryngospasm. The anaesthesiologist may have to perform an emergency surgical airway, to bypass the entire upper airway and ventilate the trachea directly. This can be a risky procedure and difficult to perform quickly and accurately.

A challenge for anesthesiologists, including emergency, intensive care and surgical physicians, is to secure a tracheal tube (intubate) rapidly without causing hypoxia. In the best case intubation may be completed within 45-60 seconds; however, patients who are predisposed to desaturation or who are not adequately pre-oxygenated (e.g. because they breathe room air between sedative/paralytic administration and achieving a secured airway) may desaturate within this time.

After surgery is completed anaesthesia is reversed. Reversal can be risky because patients begin spontaneously breathing but may continue to have a suppressed respiratory drive, reduced ability to maintain their own airway and can desaturate easily. The prosthetic airway device (e.g., the endotracheal tube) is removed during this time. As such the patient can still be largely anaesthetised without a secure airway. Oxygenation is usually provided with an open oxygen mask or low flow dry nasal cannula. Oxygen masks do not cause as much drying as a dry nasal cannula but both devices only provide oxygen for a portion of the breath and provide no pressure.

When the return of spontaneous breathing is detected at the end of anaesthesia there may also be a change in therapy. Most patients who have stable haemodynamic parameters, normal temperature, no hangover of anaesthetic or muscle paralyzing agents and adequate pain control will pose no difficulties in terms of adequate ventilation after surgery. However, in some patients, maintenance of respiratory function post-operatively can be challenging. Respiratory complications after tracheal extubation are three times more common than complications occurring during tracheal intubation and induction of anaesthesia. For example, obese patients can exhibit a rapid deterioration of gas exchange following extubation for the same reasons apparent in the pre-operative period. Reduction of aerated lung volume due to atelectasis, narrowing of small airways and difficulty in mobilizing airway secretions may lead to the so-called postoperative pulmonary restrictive syndrome, resulting in hypoxaemia. Other complications at extubation can include difficulty removing the airway device, patients biting the tracheal tube preventing its removal, which can cause further stress to the patient, airway trauma, airway obstruction and aspiration pneumonia. Laryngospasm is the most common cause of post-extubation upper airway obstruction. Post-extubation atelectasis is also a common occurrence. It has been shown that lung collapse may persist for one to four days in some patients. Nevertheless, atelectasis, even for a short period, and particularly post-extubation atelectasis, is thought to be one of the causes of the frequent incidence of post-operative hypoxemia. Moreover, particularly in patients at risk, such as the morbidly obese, atelectasis may increase the risk of pulmonary infection and contribute to later pulmonary complications such as pneumonia. These complications post-procedure can lead to a need to re-intubate the patient to ensure adequate oxygenation/ventilation. This can be costly, time-consuming and can inevitably slow the patient's recovery Further, after a period of mechanical ventilation the threshold at which the PaCO2 stimulates the return of spontaneous ventilation is increased, thus delaying the return of spontaneous ventilation. Also, the ventilatory response to acidosis is blunted, reducing a patient's ability to compensate. Anaesthetic drugs also reduce the normal protective response to hypoxia, even at low volatile drug concentrations. So as low concentrations of volatile drug may last several hours into the post-operative period, a patient may continue to be at risk of hypoxemia.

Embodiments herein address the diminished respiratory function in relation to medical procedures (before, during and after such procedures) such as anaesthesia, general anaesthesia, general anaesthesia wherein the patient is unconscious and/or procedures where tubes or scopes or other instruments are inserted into a patient's airways.

While many embodiments address a medical procedure in which there is diminished respiratory function, in certain embodiments the high gas flow therapy can also be applied to medical procedures in which there is not diminished respiratory function. For example, high gas flow can be used to provide oxygen to a mother while she is labour. This high gas flow can also be used in combination with situations in which the mother does undergo a diminished respiratory function such as, providing a mother with high gas flow to provide oxygen prior to a caesarean, during a caesarean and/or after the caesarean. The high gas flow can also be used to provide oxygen to a baby after it is born.

In accordance with at least one embodiment disclosed herein is a method of supporting respiratory function for a medical procedure with diminished or the risk of diminished respiratory function in a patient comprising promoting gas exchange with/in the patient at one or more stages of the medical procedure using high gas flow.

In some configurations promoting gas exchange comprises oxygenating the patient and/or removing CO2 from the patient and/or otherwise supporting respiratory function.

In some configurations the method comprises providing oxygenation and/or CO2 removal prior to the medical procedure.

In some configurations the method comprises providing oxygenation and/or CO2 removal during an apnoeic phase of the medical procedure.

In some configurations the method comprises providing oxygenation and/or CO2 removal after the medical procedure.

In some configurations the method comprises determining the phase of the medical procedure.

In some configurations the method comprises providing high gas flow using a high flow therapy apparatus.

In some configurations the medical procedure is anaesthesia. In some configurations, the medical procedure is general anaesthesia. In some configurations, the medical procedure is general anaesthesia wherein the patient is unconscious. In some configurations, the medical procedure involves local anaesthesia.

In some configurations the medical procedure is a partial sedation and/or conscious sedation.

In accordance with some embodiments disclosed herein is a flow therapy apparatus configured to provide oxygenation and/or CO2 removal from the patient at one or more stages of the medical procedure using high gas flow (optionally humidified). In addition, the apparatus can be optionally configured to determine the stage of the medical procedure.

In some configurations, the apparatus comprises a gas flow generator, an optional humidifier positioned downstream of the gas flow generator, the humidifier receiving gases from the gas flow generator, patient interface positioned downstream of the humidifier and a medical breathing circuit connecting the humidifier to the patient interface and configured to deliver humidified gases from the humidifier to a patient via a patient interface. A medical breathing circuit comprises one or more medical breathing tubes or conduits.

The patient interface can be any appropriate type of nasal interface, such as a cannula, a nasal mask, nasal pillows, or other type of nasal or device or combinations thereof and such patient interface can be substantially sealed, partially sealed or substantially unsealed. In some configurations, a nasal interface can be used in combination with an oral mask, a face mask or oral device (such as a tube inserted into the mouth) and/or an oral mask, a face mask or oral device (such as a tube inserted into the mouth) that can optionally be detached and/or attached to the nasal interface. Certain embodiments described herein may also find utility in combination with a patient interfaces such as oral masks and/or oral devices without a nasal interface.

In some configurations the high gas flow can be varied, for example, the gas flow can be configured to be synchronized with the patient's breathing. In some configurations, the high gas flow can be configured to include two different levels of gas flow. In some configurations, the high gas flow can be configured to include three different levels of gas flow.

In some configurations a first flow rate of gas flow is delivered during a patient inspiratory cycle and a second flow rate of gas flow is delivered during a patient expiratory cycle. In some configurations the first flow rate is at a higher flow rate than the second flow rate of gas flow.

In some configurations, a first flow rate of gas flow can be delivered at a first stage of the medical procedure, and a second flow rate of gas flow may be delivered at a second stage of the procedure. For example, a first flow rate of gas flow may be delivered during pre-oxygenation and a second flow rate of gas flow may be delivered during the apnoeic window such as during general anaesthesia and/or general anaesthesia wherein the patient is unconscious. In some configurations the second flow rate of gas flow is higher than the first flow rate of gas flow. In some configurations a third flow rate of gas flow can be delivered at a third stage of the medical procedure, for example post-operative or as the patient wakes from general anaesthesia and/or wakes from general anaesthesia wherein the patient is unconscious. In some configurations the flow rate delivered during the apnoeic window, for example, during general anaesthesia, is higher that the flow rate delivered during pre-oxygenation and/or post-anaesthesia. In some configurations, a first flow rate is provided to the patient while the patient is awake and then the flow rate is increased to a second flow rate once the patient is anesthetised. In some configurations, the first flow rate, the second flow rate and/or the third flow rate are high gas flows.

In some configurations, a first flow rate is delivered during pre-oxygenation and that flow rate is greater than 15 L/min and is up to about 90 L/min, or about 20 L/min-about 80 L/min, or about 25 L/min-about 60 L/min, or about 30 L/min-about 50 L/min, or about 40 L/min, or about 30 L/min. In an embodiment, a second flow rate is then delivered during the apnoeic window, and that flow rate is higher than during pre-oxygenation, and is about 20 L/min-about 150 L/min, or about 40 L/min-about 120 L/min, or about 50 L/min-about 100 L/min, or about 60 L/min-about 80 L/min, or about 70 L/min, or about 60 L/min. In an embodiment, the flow rate is then decreased from the flow rate during the apnoeic window to a third flow rate, wherein the lower flow rate may be less than about 90 L/min, or less than about 70 L/min, or less than about 50 L/min, or less than about 40 L/min, or less than about 20 L/min, or about 40 L/min, or about 30 L/min. The flow rate may be gradually transitioned from the second flow rate to the third flow rate.

In some configurations the first flow rate of gas flow can be delivered at a first level of anaesthesia or sedation and a flow rate of gas flow may be delivered at a second level of anaesthesia. For example, as the patient is placed under deeper anaesthesia, the flow rate is increased. In some configurations, a third flow rate of gas flow that is lower than the second flow rate can be delivered to the patient as the patient wakes. In certain arrangements, the flow rate is gradually transitioned from the higher second flow rate to the lower third flow rate. In some configurations, the first, second and/or third flow rates are high gas flows. In some configurations, the first flow rate delivered at a first level of anaesthesia or sedation greater than 15 L/min and is up to about 90 L/min, or about 20 L/min-about 80 L/min, or about 25 L/min-about 60 L/min, or about 30 L/min-about 50 L/min, or about 40 L/min, or 3 about 0 L/min. In an embodiment, a second flow rate is then delivered as the patient is placed under deeper anaesthesia, and that flow rate is higher than the first flow rate, and is about 20 L/min-about 150 L/min, or about 40 L/min-about 120 L/min, or about 50 L/min-about 100 L/min, or about 60 L/min-about 80 L/min, or about 70 L/min, or about 60 L/min. The flow rate may be gradually transitioned from the second flow rate to the third flow rate. In an embodiment, the flow rate is then decreased to a third flow rate as the patient wakes, wherein the third flow rate may be less than about 90 L/min, or less than about 70 L/min, or less than about 50 L/min, or less than about 40 L/min, or less than about 20 L/min, or about 40 L/min, or about 30 L/min. The flow rate may be gradually transitioned from the second flow rate to the third flow rate.

In some configurations, methods described herein can be used to provide pre-oxygenation and/or CO2 removal during any medical procedure that involves inserting a tube into an airway of the patient, such as for example upper endoscopies, lower endoscopies, laryngoscopies, placement of a guedel airway, placement of a laryngeal mask airway (or similar) or intubation procedures.

In some configurations the gas may be pure oxygen or a mixture of gases. In embodiments that include a mixture of gases, the mixture of gases preferably includes at least 21% oxygen and in certain arrangements can also include mixture of gases such as one or more of nitrous oxide or nitric oxide, helium, and/or air. In embodiments that include a mixture of gases, the mixture of gases preferably includes at least 90% oxygen and in certain arrangements can also include mixture of gases such as one or more of nitrous oxide or nitric oxide, helium, and/or air. In embodiments that include a mixture of gases, the mixture of gases preferably includes at least 95% oxygen and in certain arrangements can also include mixture of gases such as one or more of nitrous oxide or nitric oxide, helium, and/or air.

In accordance with at least one embodiment disclosed herein is a flow therapy apparatus configured to provide oxygenation and/or CO2 removal from the patient at one or more stages of the medical procedure using high gas flow, the apparatus optionally can be configured to determine the stage of the medical procedure. In some configuration the apparatus can adjust or change the flow rate of gas in response to determining the stage of the medical procedure.

In some configurations the apparatus comprises a gas flow generator, a humidifier positioned downstream of the gas flow generator, the humidifier receiving gases from the gas flow generator, a patient interface positioned downstream of the humidifier and a medical breathing circuit (which comprises of one or more medical breathing tubes or conduits) connecting the humidifier to the patient interface and configured to deliver humidified gases from the humidifier to a patient via a patient interface. The patient interface can be any appropriate type of nasal interface, such as a cannula, a nasal mask, nasal pillows, or other type of nasal or device or combinations thereof and such patient interface can be substantially sealed, partially sealed or substantially unsealed. In some configurations, a nasal interface can be used in combination with an oral mask, face mask or oral device (such as a tube inserted into the mouth) and/or an oral mask, face mask or oral device (such as a tube inserted into the mouth) that can optionally be detached and/or attached to the nasal interface. Certain embodiments described herein may also find utility in combination with a patient interfaces such as oral masks and/or oral devices without a nasal interface.

In some configurations the high flow can be used during various other procedures where tubes are inserted into patients such as upper endoscopies.

In some configurations the high gas flow can be humidified using a humidifier downstream of the gas flow generator. In some configurations the gas flow may be humidified to contain greater than 10 mg/L of water, greater than 20 mg/L, or greater than 30 mg/L, or up to 44 mg/L. In some configurations the gas flow may be heated to 21° C. to 42° C., or 25° C. to 40° C., or 31° C. to 37° C., or about 31° C., or about 37° C.

In some configurations the gas flow can be cyclic. It may not be a consistent high flow. In some configurations high flow is provided during the inspiration phase of the patient or during the expiration phase of the patient's respiratory cycle or some combination therein.

Accordingly, to one embodiment, a method of supporting respiratory function for a medical procedure with diminished or the risk of diminished respiratory function in a patient comprises promoting gas exchange with/in the patient at one or more stages of the medical procedure using a high gas flow that is greater than 15 L/min. In certain embodiments, the preceding method includes oxygenating the patient and/or removing CO2 from the patient and/or otherwise supporting respiratory function with the high gas flow. In any of the preceding embodiments, the method can include providing oxygenation and/or CO2 removal using high gas flow prior to the medical procedure. In any of the preceding embodiments, the method can include providing oxygenation and/or CO2 removal using high gas flow for at least 3 minutes prior to the medical procedure. In any of the preceding embodiments, the method can include providing oxygenation and/or CO2 removal using high gas flow for at least 10 minutes prior to the medical procedure. In any of the preceding embodiments, the method can include removal using high gas flow during an apnoeic phase of the medical procedure. In any of the preceding embodiments, the method can include providing oxygenation and/or CO2 removal using high gas flow after the medical procedure. In any of the preceding embodiments, the method can include a high gas flow is greater than 20 L/min, or a gas flow rate greater than 40 L/min or greater than 70 L/min. In any of the preceding embodiments, the method can include providing a high gas flow that is pure oxygen, a mixture of gases comprising at least 21% oxygen, or a mixture of gases comprising at least 21% oxygen and one or more of nitrous oxide or nitric oxide, helium, and/or air. In any of the preceding embodiments, the medical procedure can be general anaesthesia wherein the patient is unconscious. In any of the preceding embodiments, the medical procedure can be a caesarean section. In any of the preceding embodiments, the medical procedure can include a partial sedation and/or conscious sedation. In any of the preceding embodiments, the high gas flow rate can be a nasal flow delivered through nasal passages of the patient. In any of the preceding embodiments, the high gas flow rate can be supplied to the patient with a patient interface. In any of the preceding embodiments, the medical procedure the high gas flow rate can be supplied to the patient with nasal interface such as a cannula, a nasal cannula, a nasal mask, and/or nasal pillows. In any of the preceding embodiments, the high gas flow can be applied at a first flow rate before the medical procedure and a second flow rate during the medical procedure. The second flow can be greater than the first flow rate. In any of the preceding embodiments, the method can include applying a third flow rate after the medical procedure and in certain embodiments the third flow rate is less than the second flow rate. In any of the preceding embodiments, the method is used to provide oxygenation and/or CO2 removal during any medical procedure that involves inserting a tube into an airway of the patient, such as for example upper endoscopies, lower endoscopies, laryngoscopies or intubation procedures.

In any of the preceding embodiments, the medical procedure can be used to provide pre-oxygenation and/or CO2 removal prior to an anaesthetic procedure during a long enough time period to increase the apnoeic window during the apnoeic period of the anaesthetic procedure. In such an embodiment, the anaesthetic procedure can include endotracheal intubation during the apnoeic period.

In any of the preceding embodiments, the patient's head can be maintained at a first angle inclination before the medical procedure and at a second angle of inclination during the medical procedure.

In any of the preceding embodiments, the high gas flow can be humidified. In some configurations the gas flow may be humidified to contain greater than 10 mg/L of water, or greater than 20 mg/L, or greater than 30 mg/L, or up to 44 mg/L. In some configurations the gas flow may be heated to 21° C. to 42° C., or 25° C. to 40° C., or 31° C. to 37° C., or about 31° C., or about 37° C.

One embodiment comprises a high gas flow therapy apparatus configured to provide oxygenation and/or CO2 removal from the patient at one or more stages of a medical procedure using high gas flow according to any of the preceding methods. In certain embodiments, the high gas flow therapy apparatus can be configured to be used with an anaesthesia mask. In certain embodiments, the high gas flow therapy apparatus is configured to determine the stage of the medical procedure and in certain embodiment the flow therapy apparatus adjusts the flow rate delivered to the patient according to the determined stage of the medical procedure. The high gas flow apparatus can include a gas flow generator. The high gas flow apparatus can include a humidifier positioned downstream of a gas flow generator. The humidifier can receive gases from the gas flow generator. A patient interface can be positioned downstream of the humidifier and a medical breathing circuit (with associated medical breathing tubes or conduits) connecting the humidifier to the patient interface can be configured to deliver humidified gases from the humidifier to a patient via a patient interface. In certain embodiments, the high gas flow apparatus can include an interface, such as nasal cannula, nasal mask, nasal or oral device or combination thereof.

One embodiment comprises the use of a high gas flow therapy apparatus for supporting respiratory function for a medical procedure with diminished or the risk of diminished respiratory function in a patient comprising promoting gas exchange within the patient at one or more stages of the medical procedure using a high gas flow greater than 15 L/min.

One embodiment comprises a high gas flow therapy apparatus for use in providing oxygenation and/or CO2 removal from the patient at one or more stages of a medical procedure at a flow rate greater than 60 L/min.

One embodiment is a method of increasing the pressure within a patient's airway that can include preventing the collapse of a patient's anatomy and/or clearing debris or smoke during one or more stages of the medical procedure using a high gas flow that is greater than 15 L/min.

One embodiment is a method of supporting respiratory function while a patient is under general anaesthesia and the patient is unconscious. The method can include providing a high gas flow a high gas flow that is greater than 15 L/min during an apnoeic phase while the patient is under general anaesthesia and the patient is unconscious. In certain embodiments, the high gas flow is greater than 30 L/min or greater than 70 L/min. In certain embodiments, the method can also include providing a high gas flow prior greater than 15 L/min prior the putting the patient under general anaesthesia and in some embodiments the flow rate is greater than 30 L/min and in some embodiments greater than 70 L/min. Some embodiments include providing high gas flow greater than 15 L/min as the patient wakes from general anaesthesia, in some embodiments, the flow rate is greater than 30 L/min and in some embodiments, the high gas flow is greater than 70 L/min.

One embodiment is a high gas flow therapy apparatus for use in providing oxygenation and/or CO2 removal from the patient at one or more stages of a medical procedure for providing a high gas flow a high gas flow that is greater than 15 L/min during an apnoeic phase while the patient is under general anaesthesia and the patient is unconscious.

One embodiment is a method of providing ventilation while a patient is under general anaesthesia using only a gas flow delivered through a nasal interface while the patient is under general anaesthesia, the gas flow being greater than 15 L/min and in one embodiment the gas flow is greater than or equal to 30 L/min and in one embodiment the flow rate is greater than or equal to 70 L/min. In one embodiment, the patient is under general anaesthesia and unconscious.

In some embodiments, disclosed herein is a method of providing ventilation (e.g., non-invasive ventilation) while a patient is apneic under general anesthesia for an operative procedure. The method can include delivering a gas via a nasal interface to the patient at a gas flow rate of greater than 15 liters/min, wherein delivering the gas is entirely sufficient to ventilate the apneic patient without additional respiratory support. For example, the gas could be entirely sufficient to ventilate the apneic patient without endotracheal intubation. In some embodiments, delivering the gas via a nasal interface is sufficient to ventilate the apneic patient for the entirety of the operative procedure. The operative procedure can have a duration of, for example, 20 minutes. The procedure could be a caesarean section, or an endoscopic procedure for example. The gas flow rate can be, for example, greater than or equal to 30, 40, 60, 70, 80, or 90 liters/minute, or more. The gas could be at least 90% oxygen, and up to 100%, and/or humidified in some cases.

In some embodiments, disclosed herein is a method of providing ventilation (e.g. non-invasive ventilation) for a patient undergoing general anesthesia. The method can include delivering a gas via a nasal interface to the patient at a first gas flow rate prior to onset of general anesthesia. The method can also include adjusting the flow rate to a second, higher gas flow rate during general anesthesia while the patient is apneic. The second, higher gas flow rate can be maintained for the duration of the general anesthesia. The method can also include adjusting the flow rate to a third gas flow rate following general anesthesia while the patient is no longer apneic. The third gas flow rate can be different from, and in some cases less than the second gas flow rate. The first gas flow rate can be, for example, greater than or equal to 15 liters/minute. The second gas flow rate can be, for example, greater than or equal to 15, 30, 60, or 70 liters/minute. The third gas flow rate can be, for example, greater than or equal to 15 liters/minute. In some embodiments, adjusting the flow rate is accomplished via a feedback controller receiving data from a sensor. The sensor can detect pressure or carbon dioxide, for example.

In some embodiments, disclosed herein is a method of providing non-invasive ventilation for a medical procedure in a patient with diminished respiratory function or a risk of diminished respiratory function. The method can include delivering a gas via a nasal interface to the patient as a gas flow rate of greater than, for example, 60, 70, 80, 90, 100, or 120 liters/minute. The gas can be humidified. In some cases, the gas can be at least 90% oxygen, and up to 100% oxygen.

In some embodiments, disclosed herein is a system for providing non-invasive nasal ventilation to a patient during a general anesthetic operative procedure. The system can include a flow generator configured to deliver gases for oxygenating a patient via a nasal interface. The system can also include a controller configured to signal the flow generator to deliver the gases at a first predetermined flow rate. The controller can also be configured to signal the flow generator to deliver the gases at a second predetermined flow rate different from the first predetermined flow rate, depending on data received by the controller relating to the patient. In some embodiments, the controller is configured to receive data from one or more sensors and determine whether the patient is in an apneic stage or non-apneic stage. The controller can also be configured to signal the flow generator to deliver the gases at the first predetermined flow rate or the second predetermined flow rate depending on whether the patient is detected to be in the apneic stage or the non-apneic stage. In some embodiments, the sensors can be configured to detect a pressure waveform or a carbon dioxide waveform. In some embodiments, the system can also include an oxygen reservoir. The system can also be configured to non-invasively nasally ventilate the patient sufficiently for the duration of the general anesthetic operative procedure without requiring endotracheal intubation. The second predetermined flow rate can be different from the first predetermined flow rate. The controller can be further configured to receive data from the one or more sensors whether the patient has transitioned from the apneic stage to the non-apneic stage, and signal the flow generator to deliver the gases at a third predetermined flow rate. The third predetermined flow rate can be different from, such as less than the second predetermined flow rate. The second predetermined flow rate can be, for example, greater than about 60 or 70 or 90 liters/minute. The third predetermined flow rate can be, for example, greater than about 15 or 20 liters/minute. The first predetermined flow rate can be, for example, greater than about 30 liters/minute.

In some embodiments, disclosed herein is a system for providing non-invasive nasal ventilation to a patient during a general anesthetic operative procedure. The system can include a flow generator configured to deliver gases for oxygenating a patient via a nasal interface. The system can also include a controller configured to signal the flow generator to deliver the gases at a first predetermined flow rate. The first predetermined flow rate can be, for example, greater than about 60 liters/minute. The controller can be configured to receive data from one or more sensors and determine whether the patient is in an apneic stage or non-apneic stage. The controller can be configured to signal the flow generator to deliver the gases at the first predetermined flow rate or the second predetermined flow rate depending on whether the patient is detected to be in the apneic stage or the non-apneic stage. The controller can be configured to signal the flow generator to deliver the gases at the first predetermined flow rate when the patient is in the apneic stage. The controller can also be configured to signal the flow generator to deliver the gases at the second predetermined flow rate when the patient is in the non-apneic stage. In some cases, the first predetermined flow rate is greater than or equal to about 70 liters/minute. In some cases, the second predetermined flow rate is greater than or equal to about 30, or 40 liters/minute.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

This invention may also be said broadly to include the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth.

The invention includes the foregoing and also envisages constructions of which the following gives examples only.

BRIEF DESCRIPTION OF THE DRAWINGS

These and other aspects of the present disclosure will be described with reference to the following drawings, which should be considered illustrative but not limiting.

DETAILED DESCRIPTION

Figure 1:
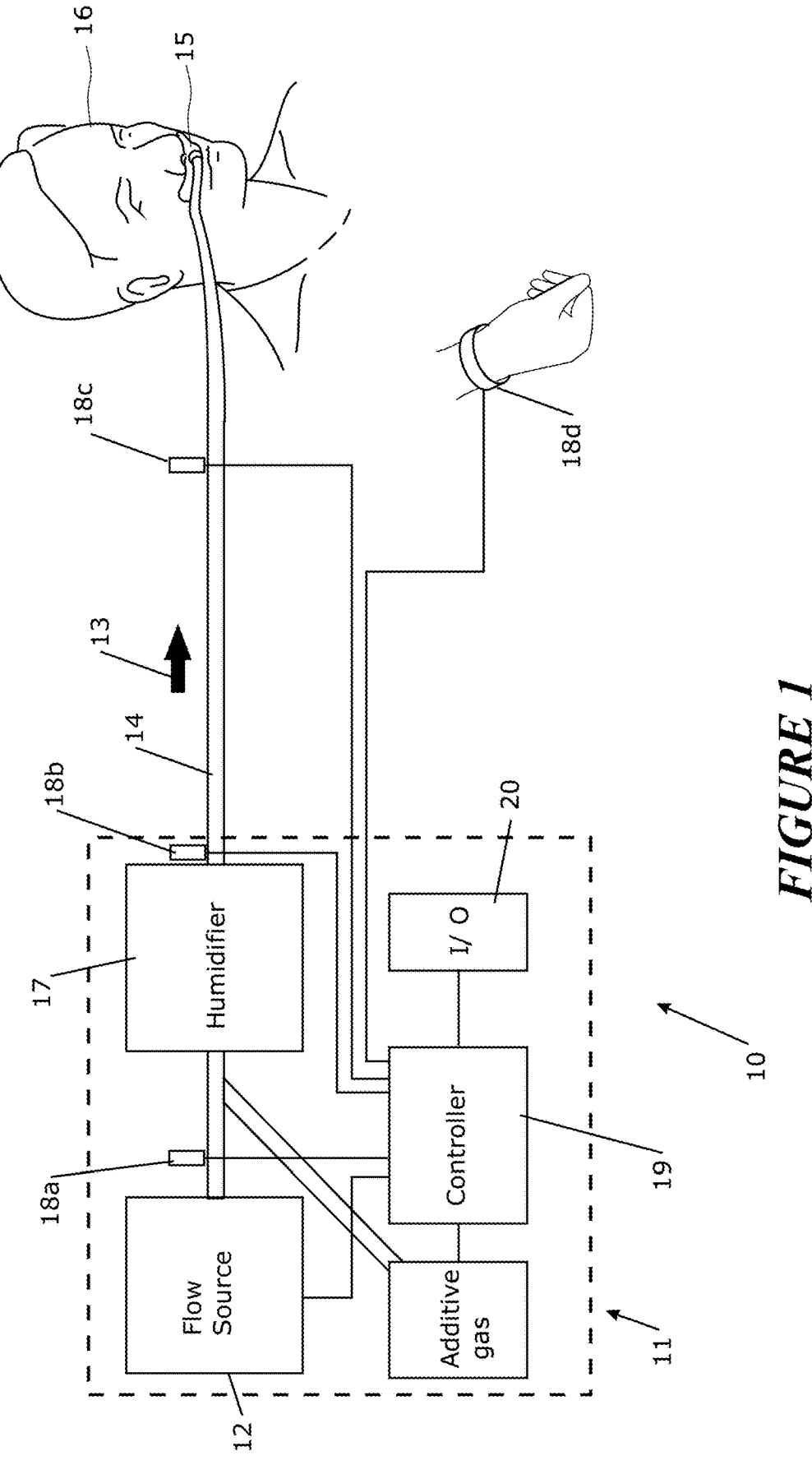
FIG. 1 illustrates an apparatus/system for oxygenating a patient/removing CO2 from a patient with high flow gas in relation to a medical procedure.

A continuous supply of oxygen is essential to sustain healthy respiratory function during medical procedures (such as during anaesthesia) where respiratory function might be compromised (e.g. diminishes or stops). When this supply is compromised, hypoxia and/or hypercapnia can occur. During medical procedures such as anaesthesia and/or general anaesthesia where the patient is unconscious, the patient is monitored to detect when this happens. If oxygen supply and/or CO2 removal is compromised the clinician stops the medical procedure and facilitates oxygen supply and/or CO2 removal. This can be achieved for example by manually ventilating the patient through an anaesthetic bag and mask. However, this is not always possible and also it delays or even possibly prevents the medical procedure taking place.

Embodiments disclosed herein address the diminished respiratory function (or risk thereof) in relation to a medical procedure (such as anaesthesia or general anaesthesia or general anaesthesia wherein the patient is unconscious) by promoting gas exchange to support respiratory function. The gas exchange respiratory function support could be across an entire medical procedure period, comprising prior to the medical procedure, during the medical procedure, and after the medical procedure (such as recovery for example). The term "medical procedure" can therefore refer to the procedure itself, or periods before, during and after as context allows. The support is provided, among other things, through providing high gas flow.

"High gas flow" or "high gas flows" as used herein is defined as the volumetric movement of a portion/parcel of gas or mixtures of gases into the patient's airways at rates exceeding the fraction of inspired oxygen requirements at peak inspiratory flow demand. In particular, in one embodiment, high gas flow (or high gas flows) refers to gas flow rate of greater than 15 L/min (Liters per minute), greater than or equal to about 20 L/min, greater than or equal to about 30 L/min, greater than or equal to about 40 L/min, greater than or equal to about 50 L/min, greater than or equal to about 60 L/min, greater than or equal to about 70 L/min, greater than or equal to about 80 L/min, greater than or equal to about 90 L/min, greater than greater than or equal to about 100 L/min, greater than about or equal to 110 L/min, greater than about or equal to 120 L/min, greater than about or equal to 130 L/min, greater than about or equal to 140 L/min or up to about 150 L/min. In certain embodiments, useful ranges of a high gas flow can be selected between any of the aforementioned flow rates including but not limited to from about 40 L/min to about 80 L/min, from about 50 L/min to about 80 L/min, from about 70 L/min to about 100 L/min, about 70 L/min to about 80 L/min, about 100 L/min to about 150 L/min and about greater than 15 L/min to about 150 L/min and about 30 L/min to about 150 L/min. These flow rates can be provided using a patient interface and in certain embodiments through a nasal interface.

A high gas flow apparatus could provide a high gas flow to a patient before, for part or all of one or more periods/stages of a medical procedure and/or after the medical procedure. High gas flow might therefore be provided for some or all or part or all of various stages of medical procedure and/or before or after the medical procedure. Without being held to any particular theory, it will be appreciated that the high gas flow can in a general sense promote gas exchange/respiratory support via at least the following mechanisms-first through the delivery of oxygen (and optionally other gas) due to the high availability of oxygen (a high FiO2), and second through the removal of CO2. Gas exchange could relate to, for example, oxygenating the patient and/or assisting CO2 removal before, during and/or after the medical procedure using a high flow of gas (such as oxygen or a mix or oxygen and one or more other gases). A medical procedure could relate, for example, to anaesthesia, where an apparatus 10 shown in FIG. 1 can be used.

Further advantages of high gas flow can include that the high gas flow increases pressure in the airways of the patient, thereby providing pressure support that opens airways, the trachea, lungs/alveolar and bronchioles. The opening of these structures enhances oxygenation, and to some extent assists in removal of CO2. The increased pressure can also keep structures such as the larynx from blocking the view of the vocal chords during intubation. When humidified, the high gas flow can also prevent airways from drying out, mitigating mucociliary damage, and reducing risk of laryngospasms and risks associated with airway drying such as nose bleeding, aspiration (as a result of nose bleeding), and airway obstruction, swelling and bleeding. Another advantage of high gas flow is that the flow can clear smoke created during surgery in the air passages. In such embodiments, the smoke can be created by lasers and/or cauterizing devices.

Referring to FIG. 1, in one embodiment, pre-oxygenation/CO2 removal (or other gas exchange) is provided prior to the medical procedure using delivery of a high flow gas. This high gas flow can pre-load the patient with oxygen so that their blood oxygen saturation level and volume of oxygen in the lungs is higher to provide an oxygen buffer while the patient is in an apnoeic phase during the medical procedure. As shown in FIG. 1, the system/apparatus 10 for providing the high gas flow could be an integrated or separate component based arrangement, generally shown in the dotted box 11 in FIG. 1. In some configurations the system 10 could be a modular arrangement of components. Hereinafter it will be referred to as system, but this should not be considered limiting. The system can include a flow source 12, such as an in-wall source of oxygen, an oxygen tank, a flow therapy apparatus, or any other source of oxygen or other gas. It may also comprise an additive gas source, comprising one or more other gases that can be combined with the flow source. The flow source 12 can provide a high gas flow 13 that can be delivered to a patient 16 via a delivery conduit 14, and patient interface 15 (such as a nasal cannula). A controller 19 controls the flow source 12 and additive gas through valves or the like to control flow, composition, concentration, volume of the high flow gas 13. A humidifier 17 is also optionally provided, which can humidify the gas under control of the controller and control the temperature of the gas. One or more sensors 18a, 18b, 18c, 18d, such as flow, oxygen, pressure, humidity, temperature or other sensors can be placed throughout the system and/or at, on or near the patient 16. The sensors can include a pulse oximeter 18d on the patient for determining the oxygen concentration in the blood.

The controller 19 can be coupled to the flow source 12, humidifier 17 and sensors 18a-18d. The controller 19 can operate the flow source to provide the delivered flow of gas. It can control the flow, pressure, composition (where more than one gas is being provided), volume and/or other parameters of gas provided by the flow source based on feedback from sensors. The controller 19 can also control any other suitable parameters of the flow source to meet oxygenation requirements. The controller 19 can also control the humidifier 17 based on feed-back from the sensors 18a-18d. Using input from the sensors, the controller can determine oxygenation requirements and control parameters of the flow source and/or humidifier as required. An input/output interface 20 (such as a display and/or input device) is provided. The input device is for receiving information from a user (e.g. clinician or patient) that can be used for determining oxygenation requirements.

Figure 4:
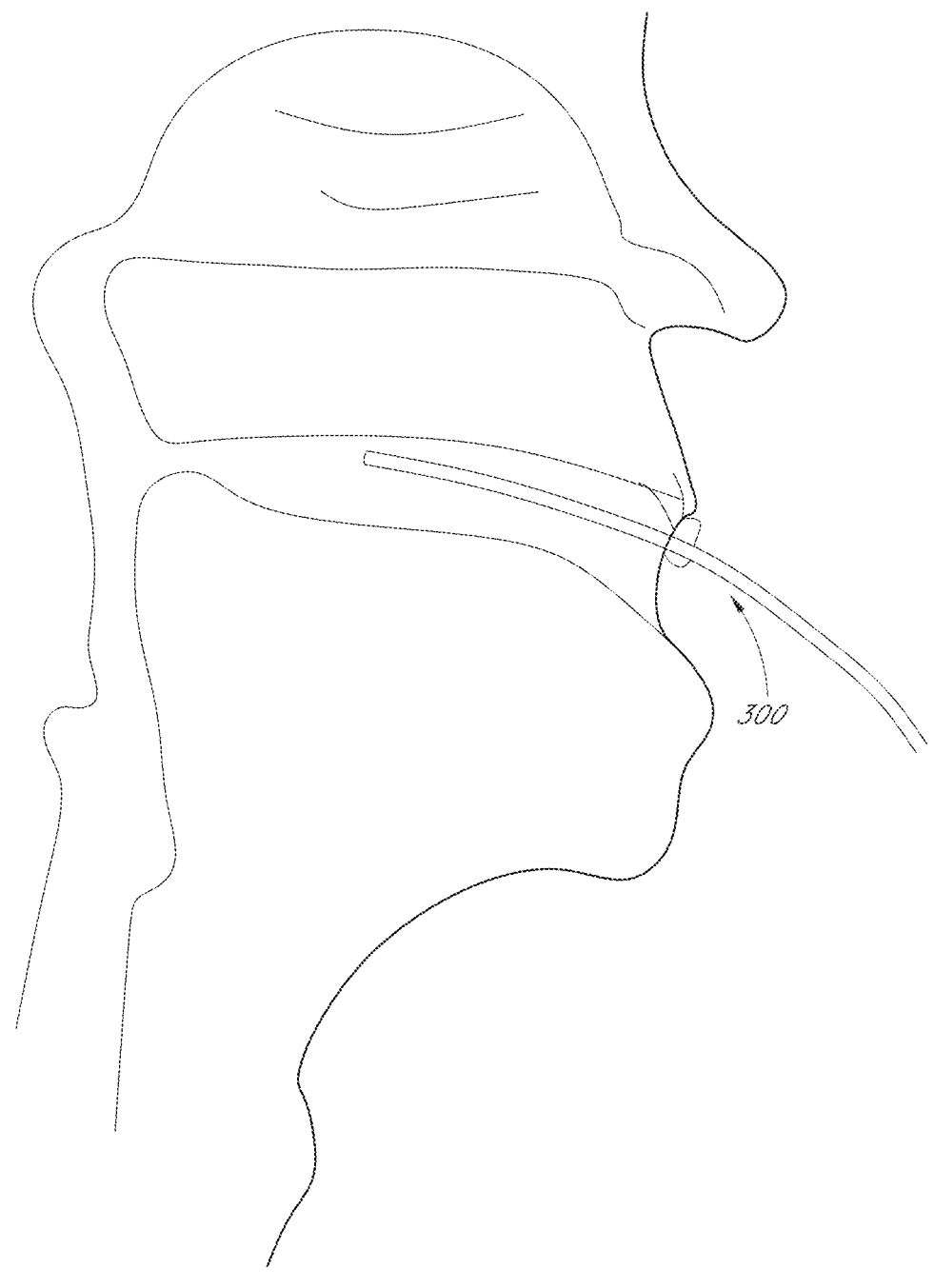
FIG. 4 illustrates delivering high flow gas with a tube in the mouth.

The pressure may also be controlled. As noted above, the high gas flow (optionally humidified) can be delivered to the patient 16 via a delivery conduit 14 and the patient interface 15 or "interface", such as a cannula, mask, nasal or oral device or combination thereof. The patient interface can be any appropriate type of nasal interface. A nasal interface as used herein is a device such as a cannula, a nasal mask, nasal pillows, or other type of nasal device or combinations thereof. The patient or nasal interface can be substantially sealed, partially sealed or substantially unsealed. A nasal interface can also be used in combination with a mask or oral device (such as a tube inserted into the mouth) and/or a mask or oral device (such as a tube inserted into the mouth) that can be detached and/or attached to the nasal interface. Certain embodiments described herein may also find utility in combination with a patient interfaces such as oral masks and/or oral devices (such as a tube inserted into the mouth as shown in FIG. 4) without a nasal interface. As used herein cannula refers to a nasal interface that includes one or more prongs that are configured to be inserted into a patient's nasal passages. A mask refers to an interface that covers a patient's mouth and/or nasal passages and can also include devices in which portions of the mask that cover the patient's mouth are removable. A mask also refers to a nasal interface that includes nasal pillows that create a substantial seal with the patient's nostrils. Nasal interfaces are particularly useful with the therapy disclosed herein and in particular nasal interfaces which allow gas flow to be administered through the nose and then pass out the mouth. The controller controls the system to provide the required oxygenation.

Certain embodiments disclosed herein are suitable for use with either a cannula or mask.

The oxygen/CO2 removal can be delivered in any of the following manners, for example.

Figure 2:
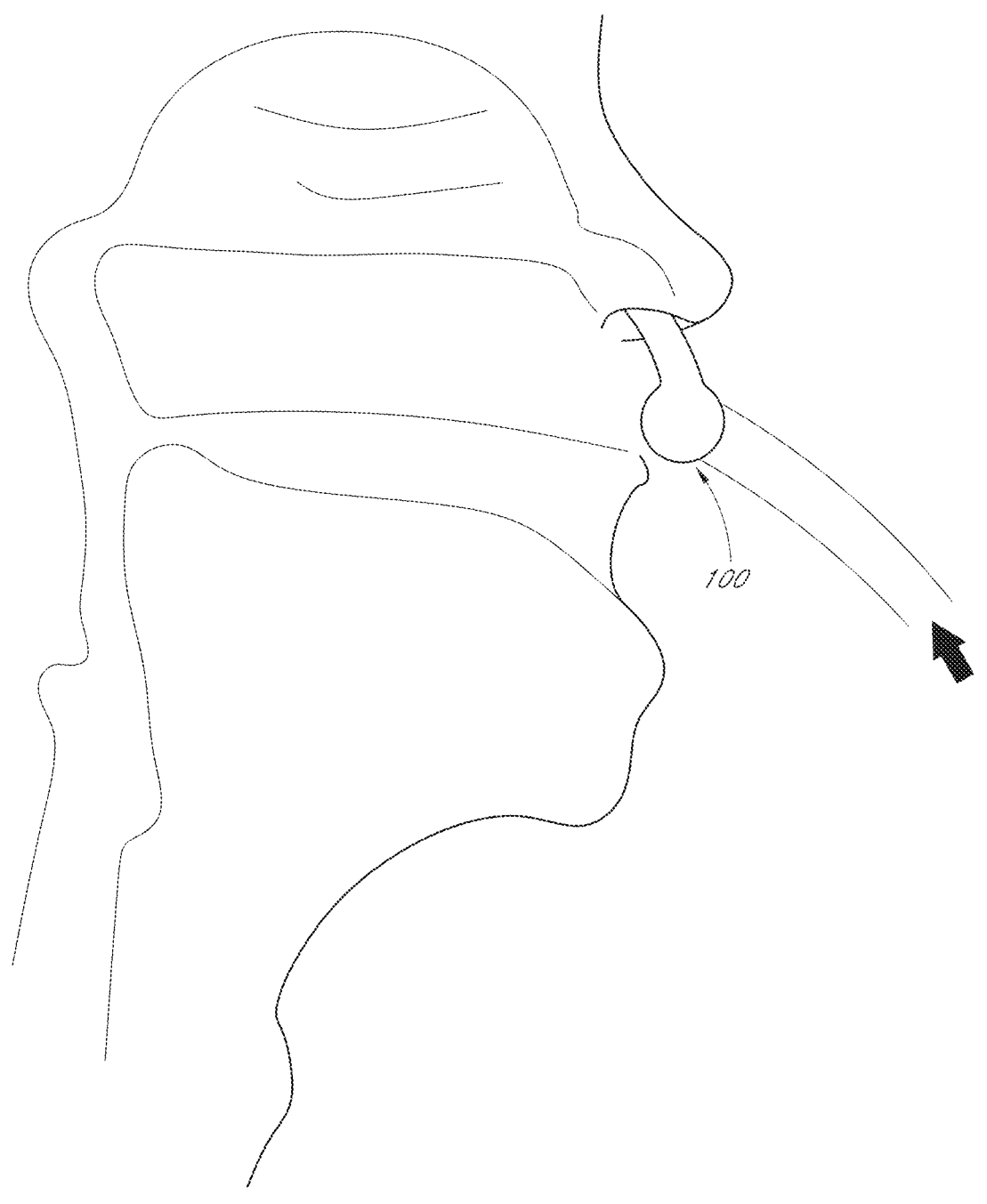
FIG. 2 illustrates delivering high flow gas with a cannula.

Referring to FIG. 2, pre-oxygenation with humidified high flows of oxygen is supplied to the patient with a nasal cannula 100.

Figure 3:
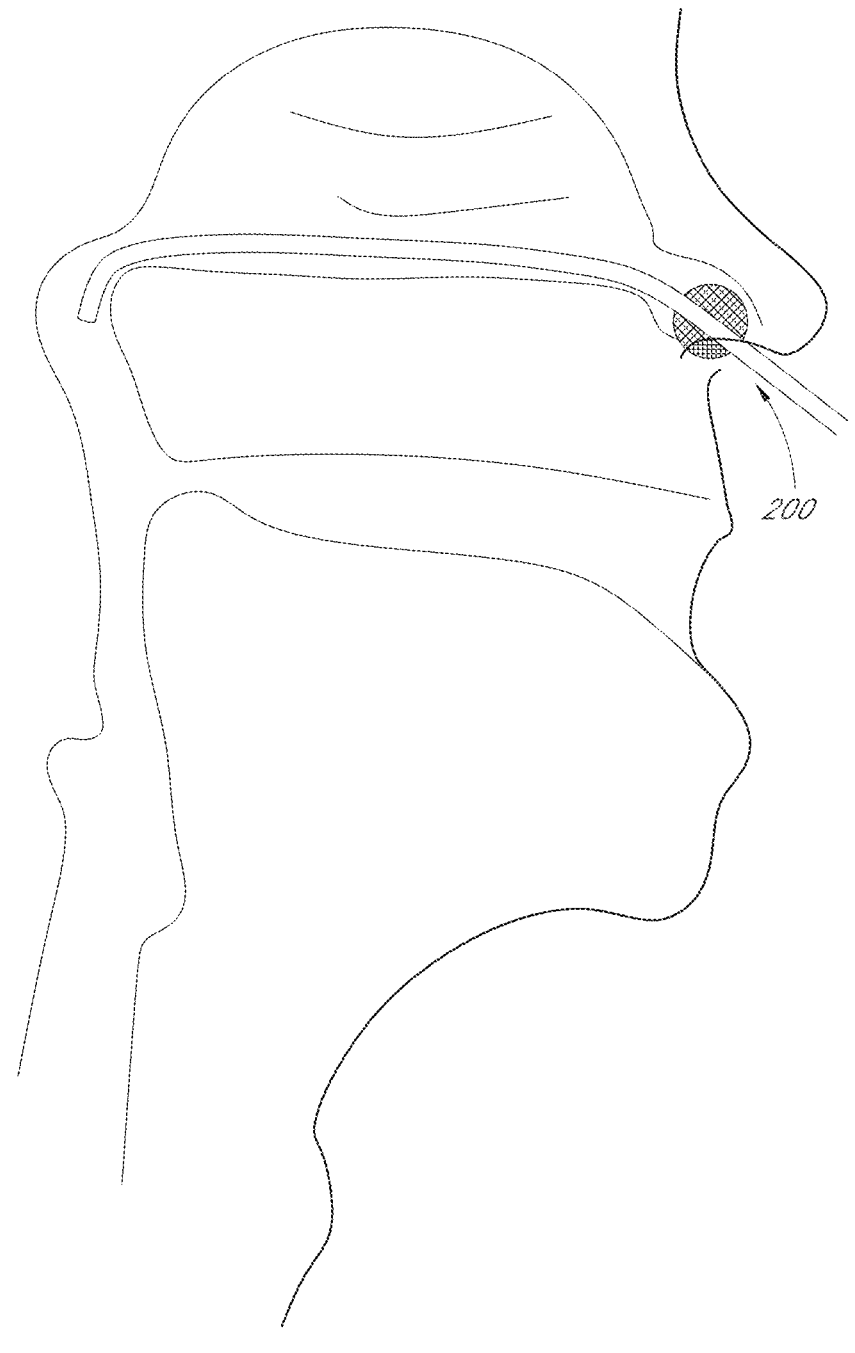
FIG. 3 illustrates delivering high flow gas with a tube in the nose.

Referring to FIG. 3, pre-oxygenation with humidified high flows of oxygen is supplied to the patient with a tube 200 inserted into the nose.

Referring to FIG. 4, pre-oxygenation with humidified high flows of oxygen is supplied to the patient with a tube 300 inserted into the mouth.

Figure 4A:
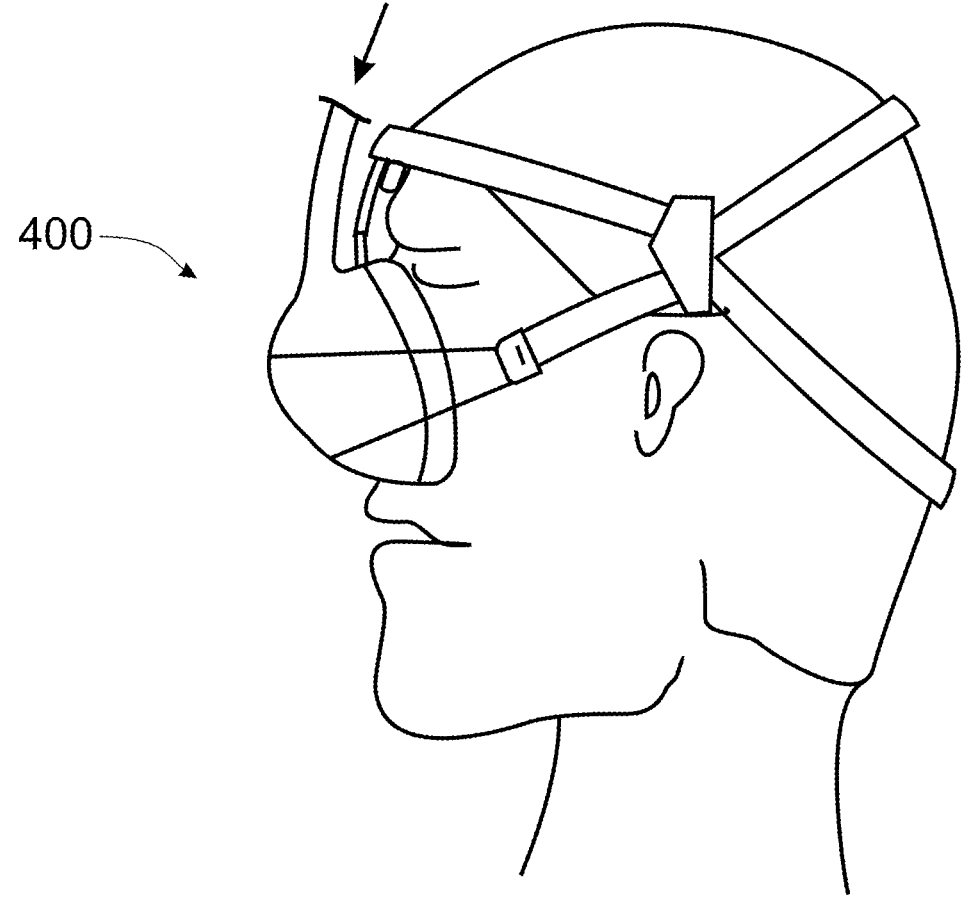
FIG. 4A illustrates delivering high flow gas with nasal mask.

Referring to FIG. 4A, pre-oxygenation with humidified high flows of oxygen is supplied to the patient with nasal mask 400.

Figure 4B:
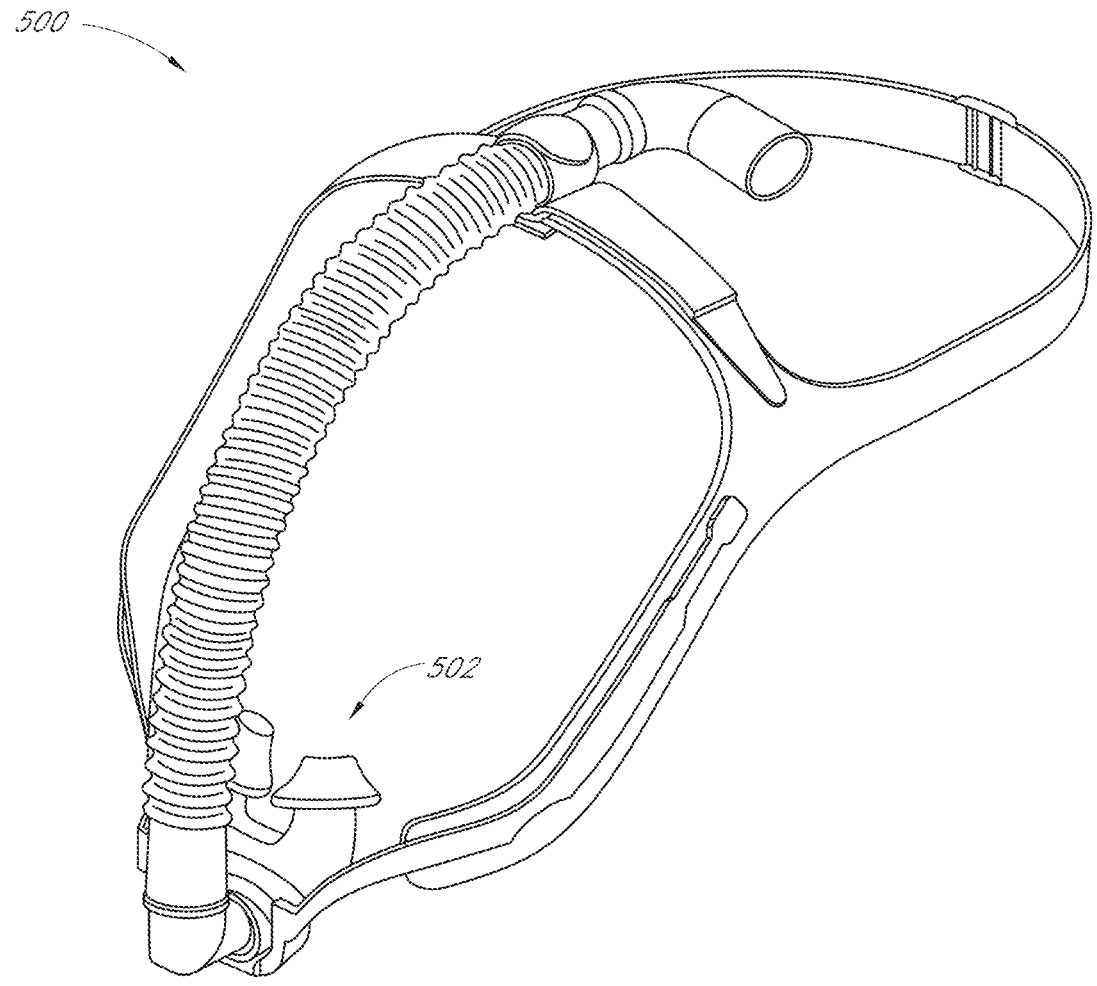
FIG. 4B illustrates a device for delivering high flow gas with nasal pillows.

FIG. 4B illustrates a device 500 with nasal pillows 502 that can be used for delivering pre-oxygenation with humidified high flows of oxygen to a patient.

Figure 5A:
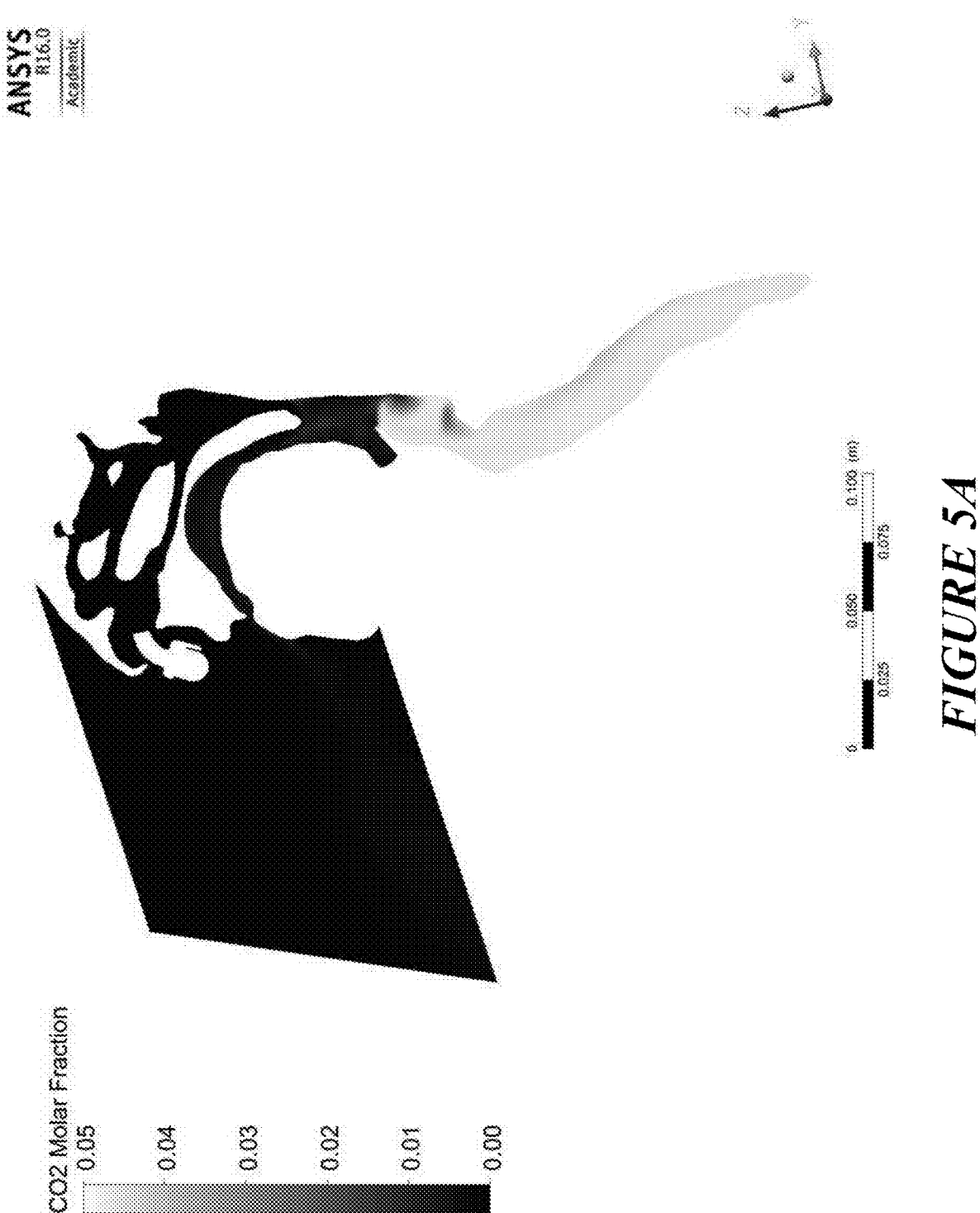
FIG. 5A illustrates computational fluid dynamics (CFD) to visualise the flow of gases in the upper airway during spontaneous breathing.

Referring to FIG. 5A, computational fluid dynamics (CFD) is shown to visualise the flow of gases in the upper airway during 60 L/min of 100% oxygen nasal flow. At the moment the patient initiates inhalation, expired gases have been flushed from the entire upper airway right down into the larynx and replaced with oxygen. This advantageously addresses an end-of expiration issue, which is a critical time as any gases in the upper airway at this time point will be part of the patient's next inspired breath. In order to minimize the amount of CO2 inhaled during the next breath it is highly beneficial that as much CO2 is flushed from the patient's airway as possible by clearing anatomical dead space with the high flow gas.

In certain embodiments, pre-oxygenation with a high gas flow can rapidly achieve full oxygenation of the patient, such that their expired breath contains no nitrogen, or over 90% oxygen or close to 100% oxygen. In some embodiments, the high gas flow may be pure oxygen or a mixture of gases. In embodiments that include a mixture of gases, the mixture of gases preferably includes at least 21% oxygen and in certain arrangements can also include mixture of gases such as one or more of nitrous oxide or nitric oxide, helium, and/or air. In embodiments that include a mixture of gases, the mixture of gases preferably includes at least 90% oxygen and in certain arrangements can also include mixture of gases such as one or more of nitrous oxide or nitric oxide, helium, and/or air. In embodiments that include a mixture of gases, the mixture of gases preferably includes at least 95% oxygen and in certain arrangements can also include mixture of gases such as one or more of nitrous oxide or nitric oxide, helium, and/or air.

This state of full oxygenation can be reached faster using high gas flow than any other technique and is technique independent as the therapy is simple to implement. Preferably, the high gas flow is also humidified. This method of pre-oxygenation can also be the most comfortable method, with improved patient compliance and reduced intubation attempts. This method also allows continuous delivery of respiratory support, even during intubation attempts. High gas flows of humidified gas, in certain embodiments, can be in the ranges and amounts described above and thus can be greater than 15 L/min (Liters per minute), greater than or equal to about 20 L/min, greater than or equal to about 30 L/min, greater than or equal to about 40 L/min, greater than or equal to about 50 L/min, greater than or equal to about 60 L/min, greater than or equal to about 70 L/min, greater than or equal to about 80 L/min, greater than or equal to about 90 L/min, greater than greater than or equal to about 100 L/min, greater than or equal to about 110 L/min, greater than or equal to about 120 L/min, greater than or equal to about 130 L/min, greater than or equal to about 140 L/min or up to about 150 L/min. In certain embodiments, useful ranges of a high gas flow can be selected between any of these aforementioned flow rates including but not limited to from about 40 L/min to about 80 L/min, from about 50 L/min to about 80 L/min, from about 70 L/min to about 100 L/min, about 70 L/min to about 80 L/min, about 100 L/min to about 150 L/min and about greater than 15 L/min to about 150 L/min and about 30 L/min to about 150 L/min. These flow rates can be provided using a patient interface and in certain embodiments through a nasal interface. In certain embodiments, humidified high gas flows of oxygen can advantageously flush the expired air from the upper airway and replace it with 100% oxygen. High gas flow can also provide increased airway pressure and/or PEEP.

In one embodiment, the high gas flow is provided to the patient for at least 30 seconds before the medical procedure, in another embodiment, at least 1 minute before the medical procedure, in another embodiment, at least 3 minutes, in another embodiment at least 5 minutes and in another embodiment at least 8 minutes and in another embodiment at least 10 minutes before the medical procedure.

In some embodiments high gas flow is provided to the patient before the apnoeic window caused by general anaesthesia and in particular general anaesthesia when the patient is unconscious. During general anaesthesia and in particular general anaesthesia when the patient is unconscious, the patient may receive a neuromuscular blockade and the patient can stop breathing and enter an "apnoeic phase", creating what is referred to as the "apnoeic window" during which to secure a definitive airway. Before the apnoeic phase caused by general anaesthesia and in particular general anaesthesia when the patient is unconscious, the patient can be provided with high gas flow in the flow rates and/or ranges described above. In one embodiment, the flow rate is equal to or greater than 70 L/min. High gas flow before the apnoeic phase caused by general anaesthesia and in particular general anaesthesia when the patient is unconscious can be particularly useful when treating patients with difficult airways (e.g. obese patients that have poor muscle tone in their airway and may be predisposed to obstructive sleep apnoea).

The apparatus and method described provides faster (than standard practice) full pre-oxygenation due to high gas flows continuously exceeding the patient's inspiratory flow and with oxygen flushing the expired air from the upper airway and replacing with 100% oxygen in some embodiments. This can enable the maximum possible reservoir of oxygen to be achieved prior to initiating apnoea. The patient's natural dead space can be reduced by 50 to 100 mls due to the flushing and turbulence created by the velocity of the oxygen into the airway. This reduces the amount of inspired $CO_2$.

The method of nasal delivery of high gas flow through for example a nasal interface to pre-oxygenate can be the most comfortable method, with improved patient compliance. The gas may also be humidified which allows higher flows than could be comfortably delivered with dry nasal delivery. Nasal delivery is also less unobtrusive compared to a face mask. These factors improve patient compliance, allowing the therapy to be delivered continuously with minimal interruption due to patient discomfort, and thus allow more effective pre-oxygenation. Nasal delivery also allows the patient to continue to talk and voice any concerns immediately prior to anaesthetisation. In contrast, masks are always visible to the patient and can obstruct the clinician's view of the patient, and talking patients cannot be understood.

Humidified oxygen flows can be provided by a patient interface. As noted above, a patient interface can be any appropriate type of nasal interface, such as a cannula (see e.g., FIG. 2), a nasal mask (see e.g., FIG. 4A), nasal pillows (see e.g., FIG. 4B), or other type of nasal or device or combinations thereof and such patient interface can be substantially sealed, partially sealed or substantially unsealed.

Face masks typically require a clinician to hold the mask firmly against the patient's face to prevent leak and entrainment of room air. This is to ensure the patient only inspires 100% oxygen (or other mixture of gases) delivered by the machine. An effective seal is difficult to achieve, due to varying facial anatomies. Further if the mask is removed due to patient complaints or needing to hear the patient talk, and the patient is allowed to breathe room air, effective pre-oxygenation can be immediately lost, requiring another period of oxygenation. A high gas flow nasal interface, such as a nasal mask, nasal pillows or nasal cannula, can advantageously remove these complications as the nasal interface is generally held on the face by headgear so that the clinician does not need to hold it and the therapy is technique independent.

Pre-oxygenation can be started sooner in the anaesthetic process with high gas flow delivered nasally relative to a face mask held by a clinician. Due to comfort and ability to talk, the patient can start pre-oxygenating during initial procedures; such as when the anaesthesiologist is confirming the patient's identity and the planned surgery. This can reduce the time required for oxygenation at induction, expediting the procedure.

The use of high gas flow through nasal delivery can provide hands-free oxygenation, unlike masks that are manually held on the patient's face, allowing anaesthesiologists to concentrate their efforts on other tasks.

In one embodiment of use, the high gas flow is provided to the patient before the medical procedure while the position of the head of the patient is in a first position (e.g., the patient's head can be at about 40 degrees of inclination). During the medical procedure, the patient's head can be at the same position or it can be changed. For example, in one arrangement, position of a head of the patient is in a second position during the medical procedure (e.g., the patient's head can be at about 20 degrees of inclination).

This method using high gas flow allows continuous delivery of respiratory support, and does not require removal for intubation attempts. The cannula or tubing embodiments can be outside of the patient's vision and allow examination of the patient's mouth in preparation for anaesthetising and intubating. The mouth can remain unobstructed and can be accessed for oral intubation. Further, respiratory support can be maintained throughout intubation attempts, reducing the chance of desaturation, and removing the need to interrupt the procedure to re-oxygenate the patient.

High gas flow also provides increased airway pressure than during natural breathing or respiratory support via a low flow gas delivery system. Increased airway pressure improves airway patency, improving clinicians' view of the airway for intubation. It also increases and maintains a patient's FRC and improves alveolar recruitment due to the delivered pressure. An increased FRC increases a patient's potential reservoir of oxygen, further increasing the time to desaturation during apnoea. This is particularly important to counteract the reduction in muscle tone at the onset of anaesthesia. Alveolar recruitment is important to ensure adequate ventilation and effective oxygenation. Ventilation with an anaesthetic bag via a standard mask is not possible during intubation because the endotracheal tube prevents appropriate access to the patient's mouth or nose.

Oxygenating the patient also may be useful during other types of periods in which the patient's breathing is stopped. For example, in certain embodiments the use of high gas flow can be applied to situations in which the patient is asked to hold their breath during a period of time such as when a CT scan is taken or other measurement of the patient is taken. Pre-oxygenation with a high gas flow as described in the embodiments herein can allow rapid oxygenation of the patient and allow the patient to hold their breath for a longer period of time.

Referring to FIG. 1 (described above), in another embodiment, oxygenation/CO2 removal is provided during the medical procedure using high gas flow delivery. The apparatus 10 of FIG. 1 (described above) can control the flow source and other aspects of the system to provide the required oxygenation and/or the high gas flow.

The oxygen/CO2 removal can be delivered in any of the following manners, for example, a patient interface can be used and the patient interface can be any appropriate type of nasal interface, such as a cannula (see e.g., FIG. 2), a nasal mask (see e.g., FIG. 4A), nasal pillows (see e.g., FIG. 4B), or other type of nasal or device or combinations thereof and such patient interface can be substantially sealed, partially sealed, or substantially unsealed. A nasal interface can also be used in combination with a face mask or oral mask or oral device (such as a tube inserted into the mouth) and/or a mask or oral device (such as a tube inserted into the mouth) that can optionally be detached and/or attached to the nasal interface. Certain embodiments described herein may also be utilized in combination with a patient interfaces such as oral masks and/or oral devices (such as a tube inserted into the mouth as shown in FIG. 4).

Figure 5B:
FIG. 5B illustrates computational fluid dynamics (CFD) to visualise the flow of gasses in the upper airway during the apnoeic period.
Figure 5B:
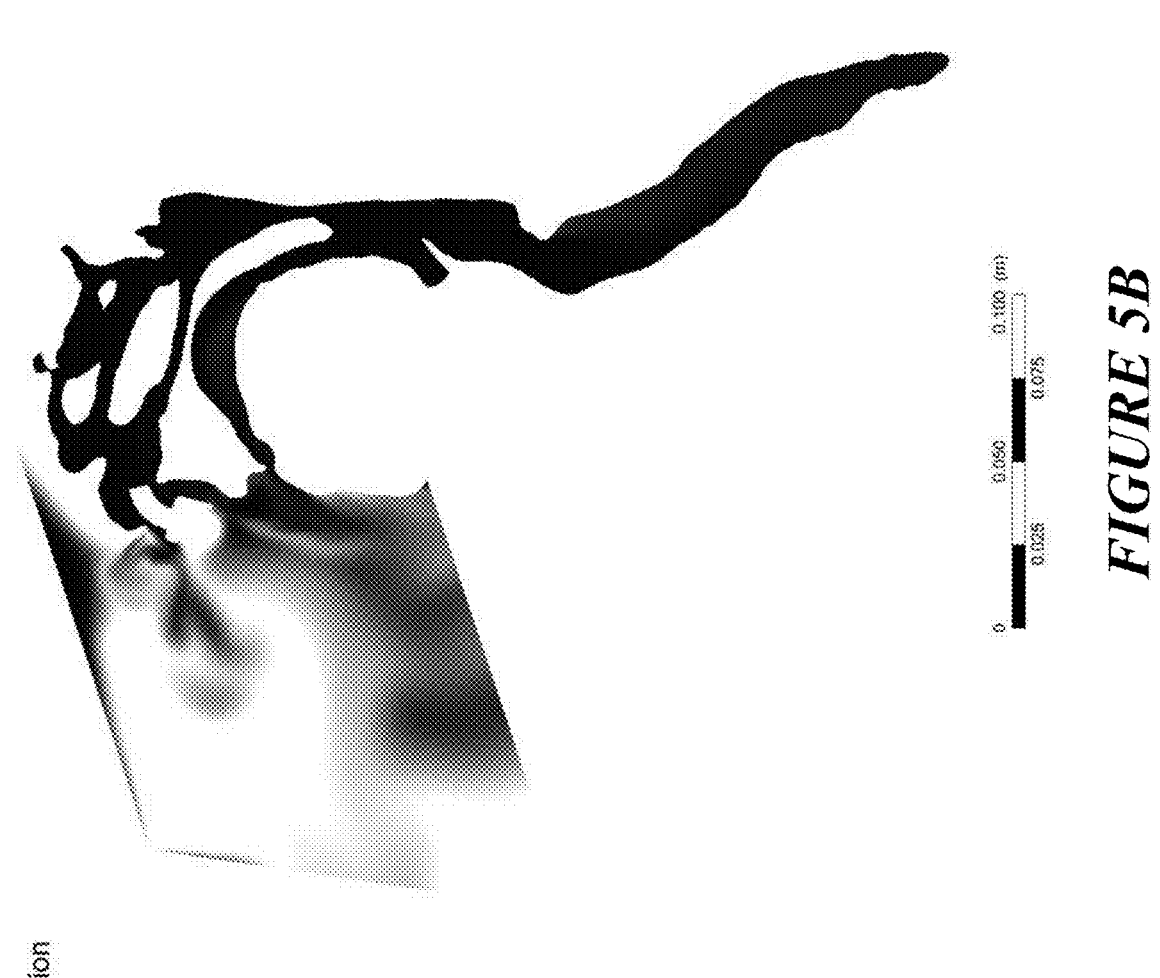
Figure 5B:
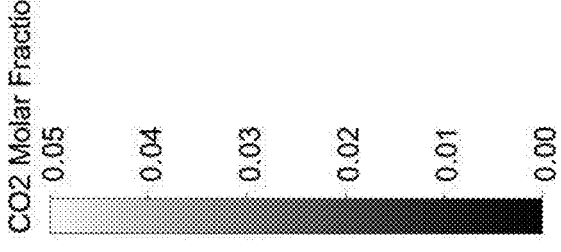

Referring to FIG. 5B, computational fluid dynamics (CFD) is shown to visualise the flow of gasses in the upper airway. FIG. 5B shows an image taken 0.3 s after nasal flow was initiated in an airway full of 0.05 CO2 Molar Fraction. This represents the CO2 concentration in the airway. The image shows CO2 is immediately flushed to the atmosphere, replaced with oxygen deep into the airway.

Figure 6:
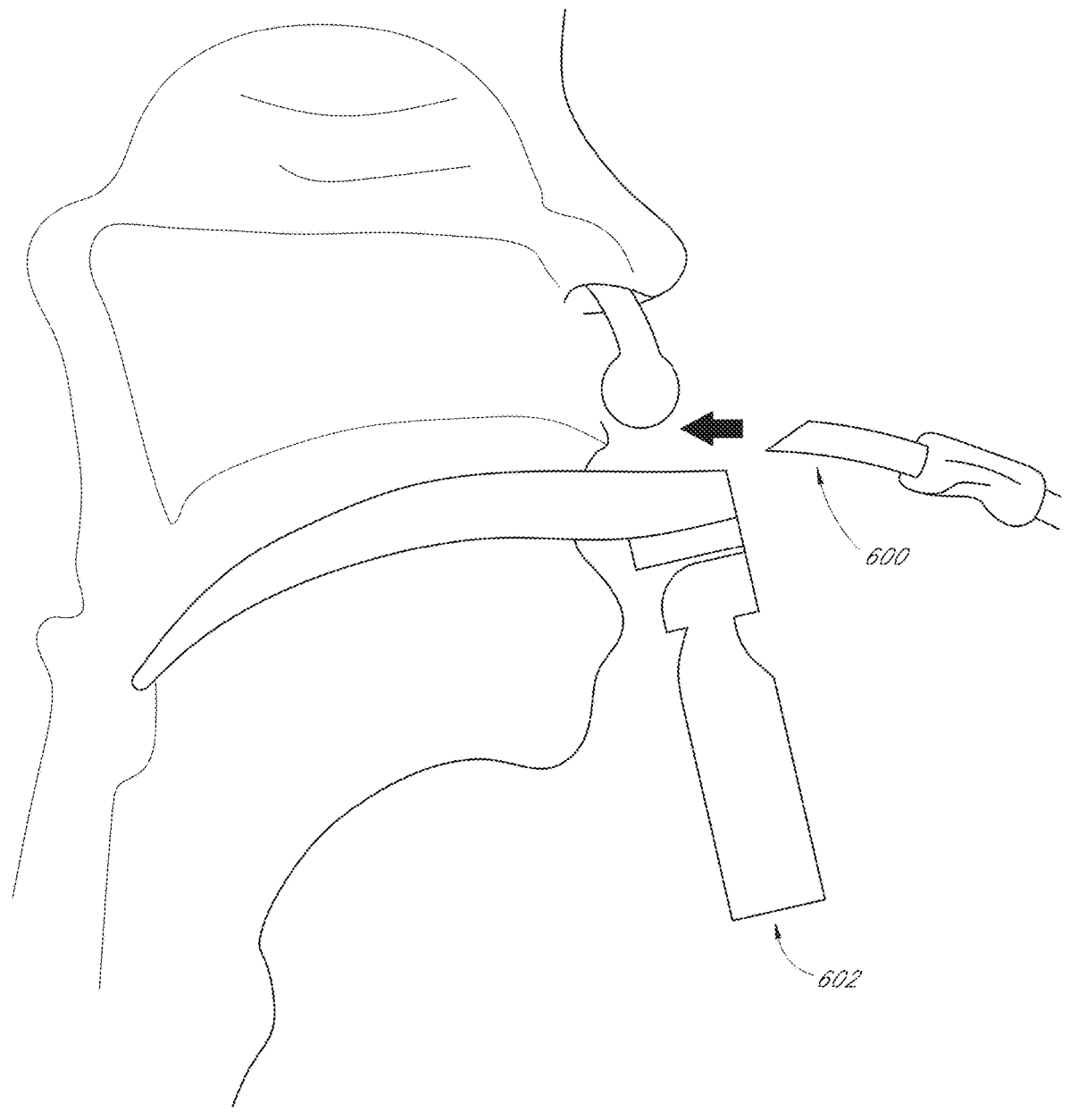
FIG. 6 illustrates intubation with Laryngoscope in place.

Referring to FIG. 6, the oxygen can be provided during the intubation procedure shown with Laryngoscope 602 in place.

Figure 7:
FIG. 7 illustrates a magnified bunch of Alveolar sacs showing perfusion.

Referring to FIG. 7, a schematic is shown of a magnified alveolus showing perfusion and gas exchange.

As noted above, the patient interface arrangements shown in FIGS. 2, 3, and 4 as above can also provide oxygenation during apnoeic phases of a medical procedure.

The therapy in one embodiment can be summarised by the following.

Oxygenating the patient also may occur during the period of apnoea by through the use of high gas flow. Removing CO2 from the airway may also occur during the period of apnoea through the use of high gas flow. The administration of high gas flow generates increased airway pressures in the airways during the period of apnoea. In certain embodiments, the humidified oxygen high gas flows can be greater than 15 L/min (Liters per minute), greater than or equal to about 20 L/min, greater than or equal to about 30 L/min, greater than or equal to about 40 L/min, greater than or equal to about 50 L/min, greater than or equal to about 60 L/min, greater than or equal to about 70 L/min, greater than about or equal to 80 L/min, greater than about or equal to 90 L/min, greater than greater than about or equal to 100 L/min, greater than or equal to about 110 L/min, greater than or equal to about 120 L/min, greater than about or equal to 130 L/min, greater than about or equal to 140 L/min or up to about 150 L/min. These flow rates can be provided using a patient interface (such as a nasal interface) that requires minimal intervention to maintain the delivery of the therapy. In certain embodiments, useful ranges of a humidified high gas flow can be selected between any of the aforementioned flow rates including but not limited from about 40 L/min to about 80 L/min, from about 50 L/min to about 80 L/min, from about 70 L/min to about 100 L/min, about 70 L/min to about 80 L/min, about 100 L/min to about 150 L/min and about greater than 15 L/min to about 150 L/min and about 30 L/min to about 150 L/min.

In some embodiments high gas flow is provided to the patient during the apnoeic window caused by general anaesthesia and in particular general anaesthesia wherein the patient is unconscious. During general anaesthesia and in particular general anaesthesia wherein the patient is unconscious, the patient may receive a neuromuscular blockade and the patient can stop breathing and enter an "apnoeic phase", creating what is referred to as the "apnoeic window" during which to secure a definitive airway. During this apnoeic phase caused by general anaesthesia and in particular general anaesthesia wherein the patient is unconscious, the patient can be provided with high gas flow in the flow rates and/or ranges described above. The flow rate may be greater than 15 L/min (Liters per minute), greater than or equal to about 20 L/min, greater than or equal to about 30 L/min, greater than or equal to about 40 L/min, greater than or equal to about 50 L/min, greater than or equal to about 60 L/min, greater than or equal to about 70 L/min, greater than about or equal to 80 L/min, greater than about or equal to 90 L/min, greater than about or equal to 100 L/min, greater than or equal to about 110 L/min, greater than or equal to about 120 L/min, greater than about or equal to 130 L/min, greater than about or equal to 140 L/min or up to about 150 L/min. In one embodiment, the flow rate is equal to or greater than 70 L/min. High gas flow during the apnoeic phase caused by general anaesthesia and in particular general anaesthesia wherein the patient is unconscious can be particularly useful when treating patients with difficult airways (e.g. obese patients that have poor muscle tone in their airway and may be predisposed to obstructive sleep apnoea).

As noted above, many general anaesthesia patients and in particular general anaesthesia wherein the patient is unconscious require placement of a definitive airway device such as an endotracheal tube or other device before the apnoeic window is ended. In some embodiments, the patient can be provided with sufficient high gas flow during the apnoeic phase such that that a definitive airway need not be established. That is, the high gas flow can be the sole or only mode of ventilation throughout the procedure. In such embodiments, the patient can be provided gas flow rates and/or ranges described above. The flow rate may be greater than 15 L/min (Liters per minute), greater than or equal to about 20 L/min, greater than or equal to about 30 L/min, greater than or equal to about 40 L/min, greater than or equal to about 50 L/min, greater than or equal to about 60 L/min, greater than or equal to about 70 L/min, greater than about or equal to 80 L/min, greater than about or equal to 90 L/min, greater than about or equal to 100 L/min, greater than or equal to about 110 L/min, greater than or equal to about 120 L/min, greater than about or equal to 130 L/min, greater than about or equal to 140 L/min or up to about 150 L/min. In one embodiment, the flow rate is equal to or greater than 70 L/min. Accordingly, certain embodiments involve providing a patient with a high gas flow during the apnoeic phase caused by general anaesthesia and in particular general anaesthesia wherein the patient is unconscious as the sole mode of ventilation during the apnoeic phase of the procedure. Certain embodiments can also involve providing a patient with a high gas flow during as the sole mode of ventilation during the apnoeic phase during a medical procedure that typically requires another mode of ventilation such as intubation and/or a bag mask. Thus in certain embodiments, the high gas flow can be provided for example with a nasal interface as the sole mode of ventilation during the entire medical procedure that typically requires another mode of ventilation such as intubation and/or a bag mask. The flow rate may be greater than 15 L/min (Liters per minute), greater than or equal to about 20 L/min, greater than or equal to about 30 L/min, greater than or equal to about 40 L/min, greater than or equal to about 50 L/min, greater than or equal to about 60 L/min, greater than or equal to about 70 L/min, greater than about or equal to 80 L/min, greater than about or equal to 90 L/min, greater than about or equal to 100 L/min, greater than or equal to about 110 L/min, greater than or equal to about 120 L/min, greater than about or equal to 130 L/min, greater than about or equal to 140 L/min or up to about 150 L/min. In one embodiment, the flow rate is equal to or greater than 70 L/min during such medical procedures. Another advantage of high gas flow is that the flow can clear smoke created during surgery in the air passages. In such embodiments, the smoke can be created by lasers and/or cauterizing devices and the clearing of the spoke can provide a better field of view during procedures on for example the ear, nose or throat.

The following 5 factors can also apply to pre-oxygenation and post-operative procedure: oxygenation, CO2 removal, airway pressure, humidity, and comfortable interface. Not to be limited by theory, but the high gas flow therapy can provide the following advantages in some embodiments:

Practical and unobtrusive-humidified high gas flows of oxygen can be delivered to the patient throughout the intubation process without affecting the practicalities and tools the anaesthesiologist is using for intubation. Arrangements such as shown in FIGS. 2, 3, 4.

High concentrations of oxygen can maximise diffusion-humidified high gas flows of oxygen during apnoea creates a concentrated reservoir of oxygen in the upper airway. This creates a steep oxygen gradient between the high concentrations in the upper airway and the concentration of oxygen in the blood at the alveolar and thus drives the diffusion of oxygen.

Reduces gas diffusion distances—the velocity and flow of the humidified high gas flows of oxygen creates turbulence, movement and mixing of gases throughout the upper airway and down into the larynx and trachea. The higher the flows, the deeper into the airway this gas mixing will occur. There is some level of mixing and bulk flow of gases occurring in the larger airways and right up to the atmosphere. This helps promote both uptake of oxygen and removal of CO2 in the alveoli.

Increased pressures in the airway-humidified high gas flows of oxygen into the airway during apnoea, increases the pressures in the airway. Pressures are typically 1 cm H2O or more. Pressure maintains alveolar recruitment and helps prevent atelectasis (collapse of the alveoli). Patency of the lower airways is maintained, so bronchioles do not collapse, which would inhibit oxygenation.

Increased airway pressure can help anaesthesiologists by keeping floppy structures in the larynx from blocking the view of the vocal cords during intubation. Increased airway pressures also help splint open the larynx, improving visualisation and oxygenation especially if the airway is narrowed or intermittently closed during bronchospasm.

Humidity-Humidity allows the comfortable delivery of higher flows. Humidity also prevents the airway from drying out, mitigating mucociliary damage, and reduces risk of laryngospasms. Humidity also reduces risks associated with airway drying such as nose bleeding, aspiration (as a result of nose bleeding), and airway obstruction, swelling and bleeding. It can also stop the laryngoscope getting stuck on skin in a dry airway, and causing trauma during procedure. In some configurations the gas flow may be humidified to contain greater than 10 mg/L of water, or greater than 20 mg/L, or greater than 30 mg/L, or up to 44 mg/L. In some configurations the gas flow may be heated to 21° C. to 42° C., or 25° C. to 40° C., or 31° C. to 37° C., or about 31° C., or about 37° C.

Maintains oxygenation throughout the apnoeic period-Safe apnoeic periods can be maintained for longer periods of time than current practice without intubation. The inventors have found that the apnoeic period can be extended to, for instance, 20 minutes without intubation and/or possibly for the duration of an operation, depending on the flow and metabolic rate. This provides a safety net during intubation and even very difficult intubations can be carried out in a stress free, methodical manner.

Carbon Dioxide can be removed from the airway throughout the apnoeic period-Flushing and mixing of gases still allows some CO2 to move to atmosphere despite the patient not spontaneously breathing. Accordingly, the apnoeic period can be extended to, for instance, 20 minutes without intubation and/or possibly for the duration of an operation, depending on the flow and metabolic rate. This provides a safety net during intubation and even very difficult intubations can be carried out in a stress free, methodical manner. Referring to FIG. 1, in another embodiment, oxygenation/CO2 removal is provided after the medical procedure using delivery of a high gas flow gas. The apparatus of FIG. 1 (described above) can control the flow source and other aspects of the system to provide the required oxygenation and/or high gas flow.

The oxygen/CO2 removal can be delivered in any of the following manners, for example a patient interface can be used and the patient interface can be any appropriate type of nasal interface, such as a cannula (see e.g., FIG. 2), a nasal mask (see e.g., FIG. 4A), nasal pillows (see e.g., FIG. 4B), or other type of nasal or device or combinations thereof and such patient interface can be substantially sealed, partially sealed or substantially unsealed. A nasal interface can also be used in combination with a mask or oral device (such as a tube inserted into the mouth) and/or a mask or oral device (such as a tube inserted into the mouth) that can be detached and/or attached to the nasal interface. Certain embodiments described herein may also find utility in combination with a patient interfaces such as oral masks and/or oral devices (such as a tube inserted into the mouth as shown in FIG. 4).

Referring to FIG. 2, oxygenation with humidified high flows of oxygen is supplied to the patient with a nasal cannula.

Referring to FIG. 3, oxygenation with humidified high gas flows of oxygen is supplied to the patient with a tube inserted into the nose. Referring to FIG. 4, oxygenation with humidified high gas flows of oxygen is supplied to the patient with a tube inserted into the mouth.

Referring to FIG. 5A, computational fluid dynamics (CFD) is used to visualise the flow of gases in the upper airway during 60 L/min of nasal flow. At the moment the patient initiates inhalation, expired gasses have been flushed from the entire upper airway right down into the larynx and replaced with oxygen.

The therapy can provide one or more of the following advantages: Faster and accurate oxygenation due to high gas flows continuously exceeding the patient's inspiratory flow and flushing the expired air from the upper airway and replacing it with fresh oxygen. This flushing is maximised at the moment the patient initiates inhalation as there is no flow to or from the lung. The patient's natural deadspace is reduced by 50 to 100 mls due to the flushing and turbulence created by the velocity of the oxygen delivered into the airway.

This method of oxygenation is the most comfortable method, with improved patient compliance. Humidification also makes flow delivery more comfortable compared with dry gas flow. This method is also unobtrusive compared to a full face mask. Cannula or tubing and/or nasal embodiments may be outside of the patient's vision and are better tolerated as the patient regains consciousness. Also, this allows the patient to talk and voice any concerns. Face masks are always visible to the patients and obstruct the clinician's view of the patient, and talking patients cannot be understood well.

Delivery of respiratory support (e.g. oxygenation) can be started before extubation. The delivered oxygen does not enter the airways until the ET tube or laryngeal mask is removed as these devices block the airway, but if the high gas flow interface is in place prior to extubation this means the pharynx is full of oxygen and oxygenation starts immediately upon extubation. Further the wakening disorientated patient is not disturbed and aggravated by having a respiratory interface applied to their face. Adequate respiratory support can help prevent respiratory deterioration which would further complicate the situation.

In this way the cannula or tubing embodiments can provide the humidified high gas flows of oxygen can remain in place throughout the surgery or procedure, to be used at times oxygen is required and there is not a secure airway with a prosthetic airway device. Such times include pre-oxygenation, apnoeic oxygenation, extubation, transport and recovery.

Increased pressures in the airway-humidified high gas flows of oxygen into the airway increases the pressures in the airway. Pressures are increased by 1 cmH2O or more.

Pressure maintains alveolar recruitment and helps prevent and treat atelectasis (collapse of the alveoli).

An increased airway pressure splints open the larynx and allows some oxygenation even if the airway is narrowed or intermittently closed during bronchospasm or laryngospasm. Patency of the lower airways is maintained, so bronchioles do not collapse. Increased airway pressures decrease incidence of obstructive apnoea, which may be especially useful in obese patients or patients with chronic obstructive apnoea.

Humidity-Humidity allows the comfortable delivery of higher flows. Additionally, both oxygen and humidity are good for wound healing, for example if airway trauma has occurred during intubation. Humidity also helps with muco-cilliary clearance via secretion mobilisation.

Once the return of spontaneous breathing has been established, delivering a high gas flow rate and/or oxygen concentration post-anaesthesia may help to reduce the inspiratory work of breathing, increase arterial oxygenation and compensate for a reduced respiratory drive that may persist post-anaesthesia.

All of these factors may also help prevent the risk of deterioration in patient condition and the need to re-intubate.

In an obstetrics situation where the mother is in labour, the foetus may be stressed and have reduced oxygen supply. Foetal distress can result in decreased oxygen saturation and may be caused by prolonged labour, poor placental blood flow as well as stress on the mother. The reduction in oxygen saturation may be due to the reduced FRC of the mother due to being pregnant and having a high metabolism.

The foetus is monitored and a decision may to be made to carry out an emergency caesarean section. There is some delay due to the need to move the patient to a theatre and assemble the personnel required, including the anaesthesiologist, surgeon, and support staff. The surgery is then undertaken, and then the baby is born and able to be oxygenated directly.

Referring to FIG. 1, in another embodiment, oxygenation/CO2 removal is provided in this situation using delivery of a high gas flow gas. The apparatus of FIG. 1 (described above) controls the flow source and other aspects of the system to provide the required oxygenation. Humidified high gas flow of oxygen given to the mother immediately when the risk of reduced oxygen in the foetus is identified can reduce the likelihood of serious oxygen desaturation in the foetus and can also provide respiratory support to the mother. The benefits of high flow described above can help mitigate the respiratory compromises suffered by the mother and in turn can improve the condition of the foetus. The mother's oxygen levels are raised to maximal levels which increases the foetus's oxygen levels. This reduces stress to the clinicians and buys the Obstetrics' team valuable time minimising the risk of irreversible damage to the baby. It may also obviate the need for a caesarean section.

This oxygenation initiation on identification of concerns of foetal desaturation merges seamlessly with pre-oxygenation for surgery.

Nasal fibreoptic intubation and rapid sequence induction (RSI) are induction/intubation techniques which are covered by the descriptions of pre-oxygenation and apnoeic oxygenation and post-procedural oxygenation.

Sedation of patients for procedures such as endoscopies or dentistry are common and reduce the patient's respiratory drive, as such humidified high gas flows of oxygen and air can provide extra oxygen to maintain oxygen saturation.

Sedation is a continuum between light sedation and pain relief to deep sedation/anaesthesia.

In certain situations, it can be easy to over sedate patients due to immense pain such as shoulder dislocation, however once popped back the pain reduces so much that the level of sedation increases markedly and the patient becomes deeply sedated or anaesthetised. In this case their respiratory drive may have already been diminished may then also become significantly more compromised and thus may benefit from the high gas flow applications described herein.

Referring to FIG. 1, in another embodiment, oxygenation/CO2 removal is provided in this situation using delivery of a high gas flow. The apparatus 10 of FIG. 1 (described above) controls the flow source and other aspects of the system to provide the required oxygenation. Humidified high gas flows of oxygen are unobtrusive and comfortable and can be used in parallel with the medical procedure. If the patient becomes apnoeic there is less concern or urgency as oxygenation and CO2 flushing can be maintained.

An example of conscious sedation is wisdom teeth removal. Such a medical procedure can have a risk of diminished respiratory function. The dental surgeon needs full access for equipment in the mouth to drill, cut and extract the teeth. Humidified high gas flows of oxygen are able to maintain oxygenation and reduce obstructive apnoeas in patients prone to them, whilst the nasal interface is unobtrusive and doesn't affect the surgeon's access.

Upper endoscopies involve inserting devices that pass through the pharynx to either the oesophagus or trachea. These patients are not only sedated but their airway is partially occluded by the device. Laryngospasm can easily be set off during upper endoscopies. As with intubations, oxygenation and CO2 flushing can be maintained by the use of humidified high gas flows of oxygen.

The embodiments above could be used alone or combination. For example, the embodiments related to procedures before a medical procedure, during the medical procedure and/or after the medical procedure could be used alone or combination.

The controller can also be configured to determine the different stages of the medical procedure (such as the pre-oxygenation phase and the apnoeic phase of anaesthesia or post-medical procedure) by monitoring the patient. This enables the controller to determine which therapy to provide. For example referring to FIG. 8 the controller can deliver oxygenation/CO2 removal, monitor the medical procedure stage, then can deliver a modified oxygenation/CO2 at when the stage changes (e.g. from pre medical procedure to during to post-medical procedure).

Figure 9:
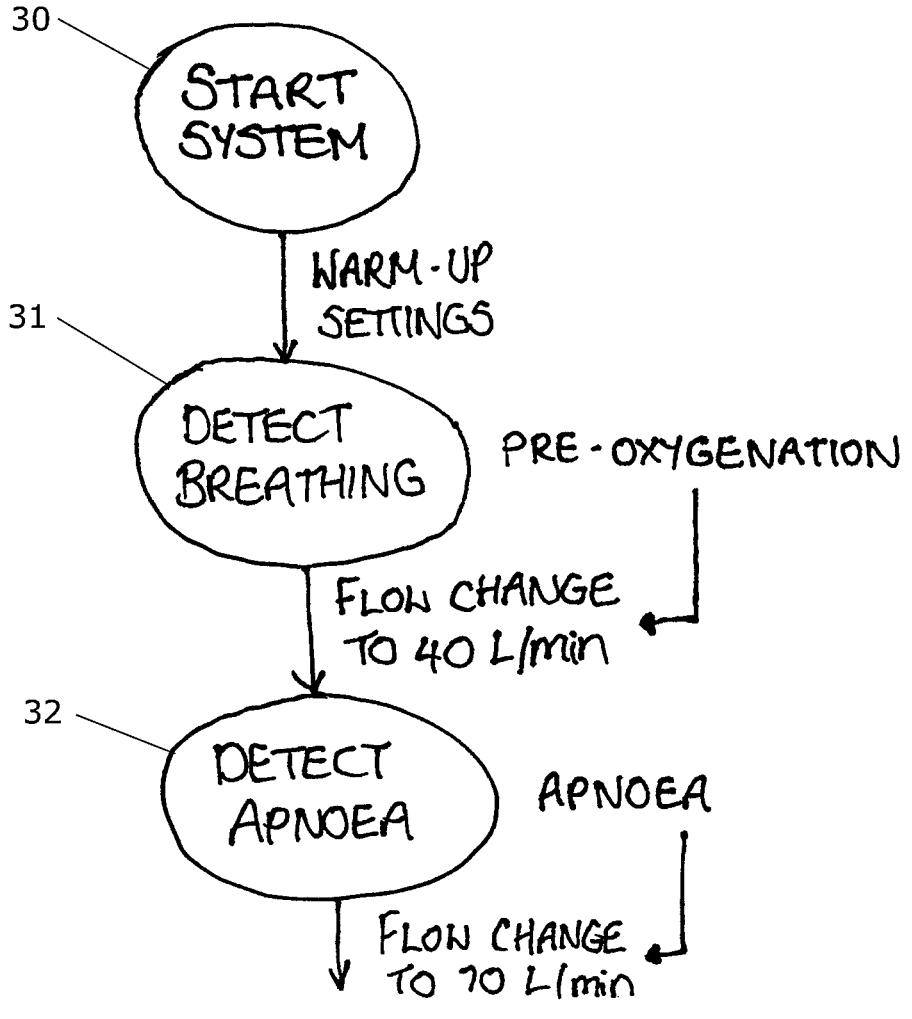
FIG. 9 illustrates a method of delivering oxygenation/CO2 removal in relation to anaesthesia.

FIG. 9 shows a particular example, in which during pre-anaesthesia breathing is detected and pre-oxygenation/CO2 removal is provided and upon detecting apnoeic stage (during anaesthesia) a modified oxygenation and/or CO2 removal is provided. More specifically, in the example provided, the high gas flow rate can be greater than 15 L/min (Liters per minute), greater than or equal to about 20 L/min, greater than or equal to about 30 L/min, greater than or equal to about 40 L/min, greater than or equal to about 50 L/min, greater than or equal to about 60 L/min, greater than or equal to about 70 L/min, greater than or equal to about 80 L/min, greater than or equal to about 90 L/min, greater than or equal to about 100 L/min, greater than or equal to about 110 L/min, greater than or equal to about 120 L/min, greater than or equal to about 130 L/min, greater than or equal to about 140 L/min or up to about 150 L/min. These flow rates can be provided using a patient interface (such as a nasal interface) that requires minimal intervention to maintain delivery of the therapy. In certain embodiments, useful ranges of a high gas flow can be selected between any of the aforementioned flow rates including but not limited from about 40 L/min to about 80 L/min, from about 50 L/min to about 80 L/min, from about 70 L/min to about 100 L/min, about 70 L/min to about 80 L/min, about 100 L/min to about 150 L/min and about greater than 15 L/min to about 150 L/min and about 30 L/min to about 150 L/min In one embodiment, a first flow rate can be provided to a patient before the medical procedure, a second flow rate can be provided to the patient during the medical procedure and a third flow rate can be provided to the patent after the medical procedure. For example, in one example arrangement, a first flow rate can be provided during a pre-oxygenation period before the medical procedure. In one arrangement, the first flow rate can be equal to greater than about 30 L/min. During the medical procedure, a second, higher flow rate can be delivered to the patient during the apnoeic window. In one arrangement, the second, higher flow rate can be equal to or greater than about 70 L/min.

Then, after the medical procedure, the flow rate can be reduced from the second flow rate to third flow rate. For example, in one embodiment, the post-medical procedure (or third) flow rate is started at 70 L/min (or other flow rate used during the medical procedure) and then gradually reduced to 30 L/min as the patient wakes. In modified embodiments, one or more of the high gas flow rate values and ranges described above can be used as the first, second and/or third flow rate used before, during and/or after the medical procedure.

Figure 8:
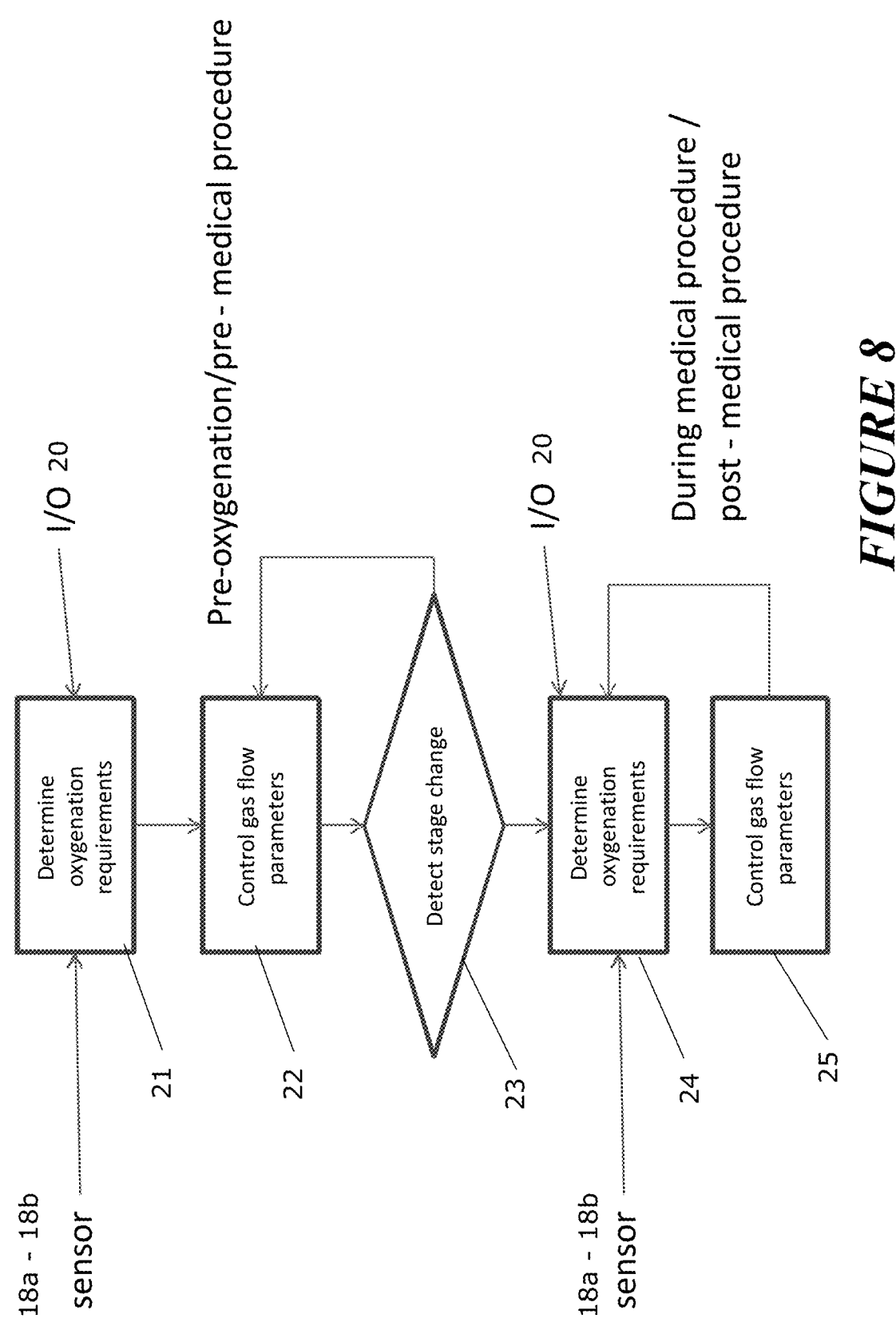
FIG. 8 illustrates a method of delivering oxygenation/CO2 removal.

With reference to FIG. 8, the controller can monitor the medical procedure stage, then the controller can be configured to deliver the first, second and/or third flow rate as described above when the stage changes (e.g. from pre medical procedure to during to post-medical procedure). For example, as shown FIG. 8 in one arrangement, during a pre-anaesthesia stage, the controller determines oxygenation requirements of the patient, step 21. These can be oxygenation requirements that are based on the prediction of what might be required before and/or during anaesthesia based on historical/empirical data. The controller 19 can receive input from the sensors 18a-18d and/or the user via the input interface 20. From that input and/or stored data (such as look up tables, historical data, parameters, relationships, the graphs or the like) the controller can determine the oxygenation requirement, step 21. The determination could take place through any processing, look up table, relationship (empirical or mathematical) or the like.

The user (such as anesthesiologist or other clinician, or the patient) provides, input via the interface 20, a pre-operative assessment to estimate the level of risk for every patient. This level of risk relates to the risk of the patient entering hypoxia during anaesthesia. The controller then determines oxygenation requirements, step 21, based on the level of risk and/or the user (e.g. anaesthesiologist or clinician) provides input indicative of the actual oxygenation requirement and/or dose/therapy settings and/or the actual parameter settings for the high flow gas delivery. Any of the input could be provided as a setting or range of settings or as one or more input values. The system could alert the user of the recommended settings or control the system to provide the settings, as to be described later.

Alternatively or additionally, and more generally, the user enters information from which oxygenation requirements can be determined, such information not necessarily directly indicating risk levels, or not being indicative of risk levels at all. Sensor input could be used alternatively or additionally.

Next, once oxygenation requirements are determined, the controller 19 operates the flow source 12, humidifier 17 and/or other aspects of the system 10 to control the parameters to provide a first flow rate of high gas flow 13 to the patient, step 22. This first flow rate is selected so that the gas flow 13 meets the oxygenation requirements during before the medical procedure (e.g., a pre-anaesthesia or pre-oxygenation stage). The first flow rate can comprise altering one or more of:

flow rate of gas (such as flow rate of oxygen)

volume of gas delivered pressure of gas composition and/or concentration of gas

Different levels of support could be optimal in different stages of the medical procedure anaesthesia. The high flow system 10 can optionally detect when a change in stage has occurred and alert the user or automatically determine new oxygenation requirements and/or change the gas flow rate to a second gas flow rate. For example, after the pre-oxygenation stage, the patient is administered the anaesthesia and enters and anaesthesia stage. Breathing function can diminish and the patient can become apnoeic. Different oxygenation requirements exist to those pre-anaesthesia. This in one embodiment a second higher gas flow rate is provided during the medical procedure.

Therefore, the controller 19 is further configured to detect the anaesthesia stage (or change in anaesthesia stage or change in medical procedure), step 23. Possible methods for detecting a change in state are as follows.

The controller uses the pressure waveform (from a pressure sensor) to detect when the patient is breathing or not (e.g. transition from pre-oxygenation to apnoea).

The controller uses the expired $CO_2$ waveform (form a sensor) to detect when the patient is breathing or not (e.g. transition from pre-oxygenation to apnoea)

While the controller 19 is monitoring the state, step 32, the high flow gas 13 is delivered as per the parameters previously determined and set. After a change in stage is determined (such as transitioning from the pre-oxygenation stage to the anaesthesia stage) the controller/system 19/10 can continue delivering gas flow 13 according to the second flow rate. However, the system 10 can also go into a monitoring phase, step 24, wherein by the oxygenation requirements are re-determined, optionally in a continuously or periodic manner, step 24. Again previous or fresh input from a user via the input interface 20 can be used to determine the oxygenation requirements, in addition or alternatively to using sensor input 18*a*-18*d*. The oxygenation requirement can be determined in the same manner as described above for the pre-oxygenation stage, with the possible difference being that it is re-determined continuously or periodically based on updated input from the sensors and/or user.

The gas flow 13 parameters are then adjusted by the controller 19 to meet new oxygen requirements, these parameters being the same as described above, step 25. Even if updated input is not received, the oxygenation requirement might be re-determined on the basis that the stage of anaesthesia had changed, or alternatively the oxygenation requirement is not specifically re-determined, but a different oxygenation requirement is presumed and the high flow gas parameters are set accordingly for the new stage.

With reference to an example embodiment of FIG. 9, in which during pre-anaesthesia breathing is detected and pre-oxygenation/$CO_2$ removal is provided and upon detecting apnoeic stage (during anaesthesia) a modified oxygenation and/or $CO_2$ removal is provided. With reference to FIG. 9, after the system started, step 30, the system monitors the patient and detects breathing, step 31, and determines a pre-oxygenation stage. The system provides high gas flow, including a flow rate of 40 L per minute, which are suitable for the pre-oxygenation stage, based on typical oxygenation requirements. After further monitoring of the patient, the system detects an apnoea, and assumes that the anaesthesia stage has started, step 32. That changes the parameters of the high gas flow to a higher flow rate such as a flow rate of 70 L per minute which meets the oxygenation requirements of the apnoeic stage, step 32. In one arrangement, the flow rate in the oxygenation stage can be equal to greater than about 30 L/min. During the medical procedure, a second, higher flow rate can be delivered to the patient during the apnoeic window. In one arrangement, the second, higher flow rate in the apnoeic stage can equal to or greater than about 70 L/min. Then, after the medical procedure, the flow rate can be reduced from the second flow rate to third flow rate. For example, in one embodiment, the post-medical procedure (or third) flow rate is started at 70 L/min (or other flow rate used during the medical procedure) and then gradually reduced to 30 L/min as the patient wakes. In these example embodiments, the apnoeic stage can be caused by placing the patient under general anaesthesia and in certain embodiments general anaesthesia where the patient is unconscious.

As relatively high gas delivery flow rates may be used with the embodiments or configurations described herein, the gases being supplied or delivered to the user or patient can be delivered to different parts of the user's or a patient's airway. However, as noted above, in certain embodiments, it is advantageous to provide the high gas flow through a nasal interface.

For example, according to those various embodiments and configurations described herein, a high gas flow of gases supplied or provided to an interface or via a system, such as through a nasal interface, may comprise, but is not limited to the high gas flow rates and ranges described above, such as, for example, flow rates of greater than 15 L/min (Liters per minute), greater than or equal to about 20 L/min, greater than or equal to about 30 L/min, greater than or equal to about 40 L/min, greater than or equal to about 50 L/min, greater than or about equal to 60 L/min, greater than or about equal to about 70 L/min, greater than or about equal to about 80 L/min, greater than or about equal to about 90 L/min, greater than or equal to about 100 L/min, greater than or equal to about 110 L/min, greater than or equal to about 120 L/min, greater than or equal to about 130 L/min, greater than or equal to about 140 L/min or up to about 150 L/min. These flow rates can be provided using a patient interface (such as a nasal interface) that requires minimal intervention to maintain the delivery of the therapy. In certain embodiments, useful ranges of a high gas flow can be selected between any of the aforementioned flow rates including but not limited from about 40 L/min to about 80 L/min, from about 50 L/min to about 80 L/min, from about 70 L/min to about 100 L/min, about 70 L/min to about 80 L/min, about 100 L/min to about 150 L/min and about greater than 15 L/min to about 150 L/min and about 30 L/min to about 150 L/min As noted above FIG. 1 (described in more detail above) illustrates an apparatus/system 10 for oxygenating a patient/removing $CO_2$ from a patient with high flow gas in relation to a medical procedure. In certain embodiments, the apparatus/system 10 is configured to be used a surgical environment such that it can be used in surgical procedures. In certain embodiments, the apparatus/system 10 is configured to provide high gas flow rates at the rates and/or within the ranges described above. In one embodiment, apparatus/ system 10 is configured to provide a high gas flow while a patient is under general anaesthesia and in particular general anaesthesia where the patient is unconscious using only a high gas flow delivered through a nasal interface while the patient is under general anaesthesia. In one embodiment, the gas flow being greater than 15 L/min and in another embodiment greater than 60 L/min. In certain embodiments, apparatus/system 10 is configured to provide high gas flow for use in providing oxygenation and/or CO2 removal from the patient at one or more stages of a medical procedure at flow rate that is greater than 15 L/min during an apnoeic phase while the patient is under general anaesthesia and in particular general anaesthesia where the patient is unconscious.

The terms "approximately", "about", and "substantially" as used herein represent an amount or characteristic close to the stated amount or characteristic that still performs a desired function or achieves a desired result. For example, the terms "approximately", "about", and "substantially" may refer to an amount in certain embodiments that is within less than plus or minus 10% of, within less than plus or minus 5% of, within less than plus or minus 1% of, within less than plus or minus 0.1% of, and within less than plus or minus 0.01% of the stated amount or characteristic.

Figure 10:
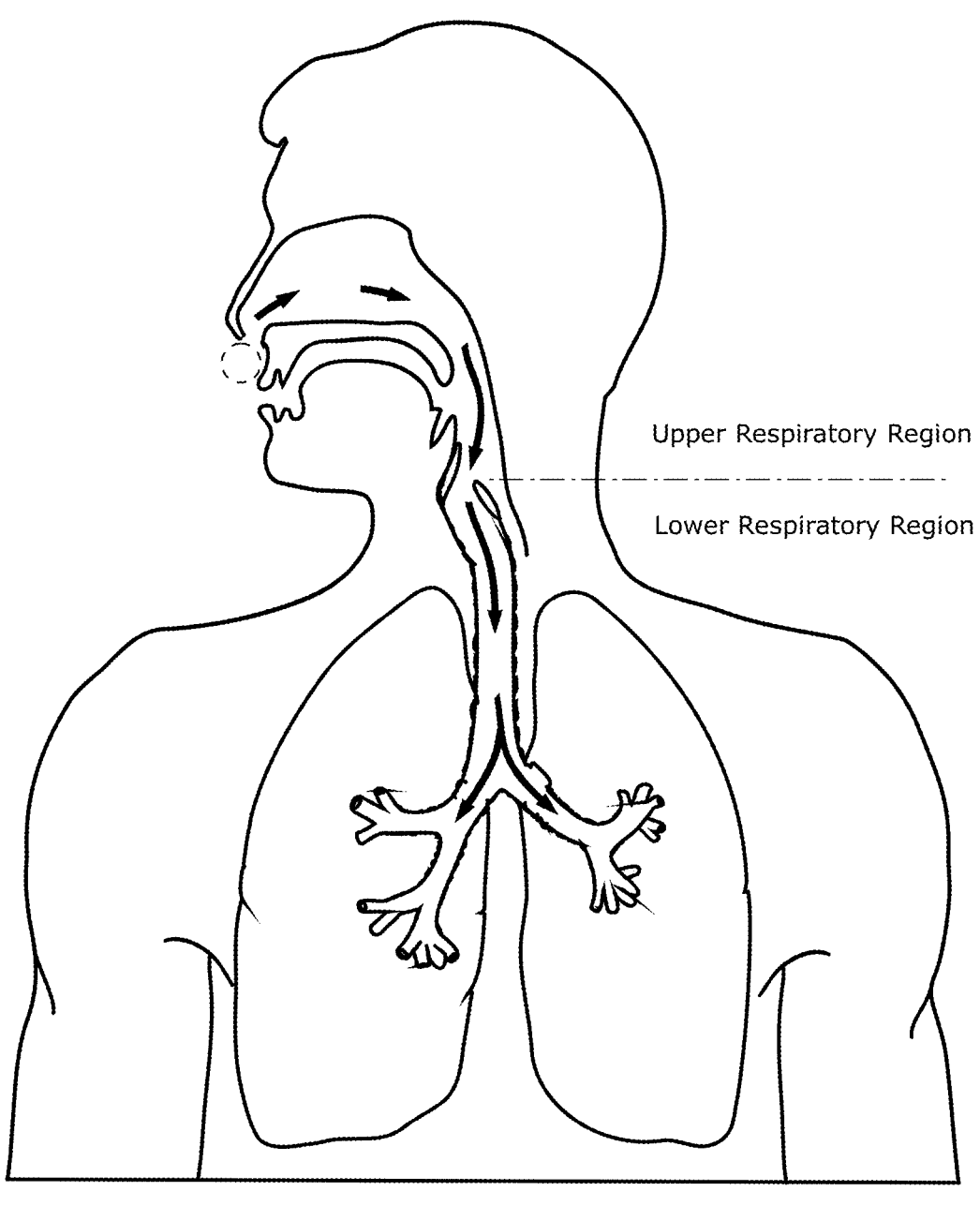
FIG. 10 illustrates the airways of a patient.

Such relatively high gas flow rates of gases may assist in providing the supplied gases into a user's airway, or to different parts of a user's airway, for example such flow rates may allow for a delivery of such gases to the upper or lower airway regions, such as shown in FIG. 10. The upper airway region typically includes the nasal cavity, pharynx and larynx, while the lower airway region typically includes the trachea, bronchi and lungs.

The following example embodiments with reference to clauses identify some possible permutations of combinations of features disclosed herein, although other permutations of combinations of features are also possible including those described in the claims.

Clause 1. A method of supporting respiratory function for a medical procedure with diminished or the risk of diminished respiratory function in a patient comprising promoting gas exchange with/in the patient at one or more stages of the medical procedure using high gas flow.

Clause 2. A method according to Clause 1 wherein promoting gas exchange comprises oxygenating the patient and/or removing CO2 from the patient and/or otherwise supporting respiratory function Clause 3 A method according to Clause 2 comprising providing oxygenation and/or CO2 removal prior to the medical procedure.

Clause 4. A method according to Clause 2 comprising providing oxygenation and/or CO2 removal during an apnoeic phase of the medical procedure.

Clause 5. A method according to Clause 2 comprising providing oxygenation and/or CO2 removal after the medical procedure.

Clause 6. A method according to any preceding Clauses comprising determining the phase of the medical procedure.

Clause 7. A method according to any preceding Clauses comprising providing high gas flow using a high flow therapy apparatus.

Clause 8. A method according to any preceding Clauses wherein the medical procedure is anaesthesia.

Clause 9. A method according to any preceding Clauses wherein the medical procedure is a caesarean section.

Clause 10. A method according to any preceding Clauses wherein the medical procedure is a partial sedation and/or conscious sedation.

Clause 11. A flow therapy apparatus configured to provide oxygenation and/or CO2 removal from the patient at one or more stages of the medical procedure using high gas flow (optionally humidified), the apparatus optionally configured to determine the stage of the medical procedure.

Clause 12. A flow therapy apparatus according to Clause 11 wherein the apparatus comprises a gases flow generator, an optional humidifier positioned downstream of the gases flow generator, the humidifier receiving gases from the gases flow generator, an unsealed patient interface positioned downstream of the humidifier and a medical circuit connecting the humidifier to the patient interface and configured to deliver humidified gases from the humidifier to a patient via a patient interface.

Clause 13. An apparatus according to Clause 12 further comprising a cannula, such as nasal cannula, nasal mask, nasal or oral device or combination thereof.

Clause 14. A method according to any one of the Clauses 1 to 10 wherein the gas may be pure oxygen or a mixture of gases.

Clause 15. A method according to any one of Clauses 1 to 10 and 14 wherein the high gas flow can be an synchronized with the patient's breath, the gases flow configured to vary between a first gases flow and a second gases flow.

Clause 16. A method according to Clause 15 wherein the first gases flow is delivered during a patient inspiratory cycle and the second gases flow is delivered during a patient expiratory cycle.

Clause 17. A method according to any one of Clauses 1 to 10 and 14 to 16 wherein the method is used to provide pre-oxygenation and/or CO2 removal during any medical procedure that involves inserting a tube into an airway of the patient, such as for example upper endoscopies, lower endoscopies, laryngoscopies or intubation procedures.

Clause 18. A method of supporting respiratory function for a medical procedure with diminished or the risk of diminished respiratory function in a patient comprising promoting gas exchange with/in the patient at one or more stages of the medical procedure using a high gas flow that is at greater than 15 L/min.

Clause 19. A method according to clause 18 wherein promoting gas exchange comprises oxygenating the patient and/or removing CO2 from the patient and/or otherwise supporting respiratory function with the high gas flow.

Clause 20. A method according to any of clauses 18-19, further comprising providing oxygenation and/or CO2 removal using high gas flow prior to the medical procedure.

Clause 21. A method according to Clause 20 comprising providing oxygenation and/or CO2 removal using high gas flow for at least 3 minutes prior to the medical procedure.

Clause 22. A method according to Clause 21 comprising providing oxygenation and/or CO2 removal using high gas flow for at least 10 minutes prior to the medical procedure.

Clause 23. A method according to any of Clauses 18-22, further comprising providing oxygenation and/or CO2 removal using high gas flow during an apnoeic phase of the medical procedure.

Clause 24. A method according to any of Clauses 18-23 comprising providing oxygenation and/or CO2 removal using high gas flow after the medical procedure.

Clause 25. A method according to any of claims 18-24 wherein the high gas flow is greater than 20 L/min.

Clause 26. A method according to any of claims 18-25 wherein the high gas flow is greater than 40 L/min.

Clause 26. A method according to any of Clauses 18-26 wherein the high gas flow is greater than 70 L/min, or greater than 80 L/min, or greater than 90 L/min, or greater than 100 L/min, or less than 150 L/min.

Clause 27. A method according to any of Clauses 18-27, wherein the high gas flow is pure oxygen, a mixture of gases comprising at least 21% oxygen, or a mixture of gases comprising at least 21% oxygen and one or more of nitrous oxide or nitric oxide, helium, and/or air.

Clause 28. A method according to any of Clauses 18-27, wherein the high gas flow is pure oxygen, a mixture of gases comprising at least 21% oxygen, or a mixture of gases comprising at least 21% oxygen and one or more of nitrous oxide or nitric oxide, helium, and/or air.

Clause 29. A method according to any of Clauses 18-28, wherein the medical procedure is general anaesthesia and the patient is unconscious.

Clause 30. A method according to any of Clauses 18-29, wherein the medical procedure is a caesarean section.

Clause 31. A method according to any of Clauses 18-30, wherein the medical procedure is a partial sedation and/or conscious sedation.

Clause 32. A method according to any of Clauses 18-31, wherein the high gas flow rate is nasal flow delivered through nasal passages of the patient.

Clause 33. A method according to any of Clauses 18-32, wherein the high gas flow rate is supplied to the patient with a patient interface.

Clause 34. A method according to any of Clauses 18-33, wherein the high gas flow rate is supplied to the patient with nasal interface such as a cannula, a nasal mask, and/or nasal pillows.

Clause 35. A method according to any of Clauses 18-34, wherein the high gas flow is applied at a first flow rate before the medical procedure and a second flow rate during the medical procedure.

Clause 36. A method according to clause 35 wherein the second flow rate is greater than the first flow rate.

Clause 37. A method according to clause 35 or 36 further comprising applying a third flow rate after the medical procedure.

Clause 38. A method according to clause 37 wherein the third flow rate is less than the second flow rate.

Clause 39. A method according to any of clauses 35 to 38, wherein the first flow rate is 15 L/min-90 L/min, or 20 L/min-80 L/min, or 25 L/min-60 L/min, or 30 L/min-50 L/min, or 40 L/min, or 30 L/min, and the second flow rate is 20 L/min-150 L/min, or 40 L/min-120 L/min, or 50 L/min-100 L/min, or 60 L/min-80 L/min, or 70 L/min, or 60 L/min.

Clause 40. A method according to clause 39 further comprising applying a third flow rate after the medical procedure wherein the third flow rate is less than 90 L/min, or less than 70 L/min, or less than 50 L/min, or less than 40 L/min, or less than 20 L/min, or 40 L/min, or 30 L/min.

Clause 41. A method according to clauses 37 or 39 wherein the third flow rate is less than the second flow rate and the flow rate is gradually transitioned from the second flow rate to the third flow rate.

Clause 42. A method according to any to any of Clauses 18-41 wherein the method is used to provide oxygenation and/or CO2 removal during any medical procedure that involves inserting a tube into an airway of the patient, including upper endoscopies, endoscopies, laryngoscopies or intubation procedures.

Clause 43. A method according to any to any of Clauses 18-42 wherein the method is used to provide pre-oxygenation and/or CO2 removal prior to an anaesthetic procedure during a long enough time period to increase the apnoeic window during the apnoeic period of the anaesthetic procedure.

Clause 44. A method according to clause 43 wherein the anaesthetic procedure comprises endotracheal intubation during the apnoeic period.

Clause 45. A method according to any of Clauses 18-44 wherein the patient's head is maintained at a first angle inclination before the medical procedure and at a second angle of inclination during the medical procedure.

Clause 46. A method according to any to any of clauses 18-45 wherein the high gas flow is humidified.

Clause 47. A high gas flow therapy apparatus configured to provide oxygenation and/or CO2 removal from the patient at one or more stages of a medical procedure using high gas flow according to any of Clauses 18-46.

Clause 48. The high gas flow therapy apparatus of clause 47 configured to be used with an anaesthesia mask.

Clause 49. The high gas flow apparatus according to clause 47 configured to determine the stage of the medical procedure.

Clause 50. The high gas flow apparatus according to clause 49 wherein the flow therapy apparatus adjusts the flow rate delivered to the patient according to the determined stage of the medical procedure.

Clause 51. The high gas flow apparatus according to any of clauses 47 to 51 wherein the apparatus comprises a gas flow generator.

Clause 52. The high gas flow apparatus according to any of clauses 47-51 wherein the apparatus comprises humidifier positioned downstream of the gas flow generator, the humidifier receiving gases from the gas flow generator, a patient interface positioned downstream of the humidifier and a medical breathing circuit connecting the humidifier to the patient interface and configured to deliver humidified gases from the humidifier to a patient via a patient interface.

Clause 53. The high gas flow apparatus according to any of clauses 47-52 further comprising an interface, such as nasal cannula, nasal mask, nasal or oral device or combination thereof.

Clause 54. The use of a high gas flow therapy apparatus for supporting respiratory function for a medical procedure with diminished or the risk of diminished respiratory function in a patient comprising promoting gas exchange within the patient at one or more stages of the medical procedure using a high gas flow greater than 15 L/min.

Clause 55. A high gas flow therapy apparatus for use in providing oxygenation and/or CO2 removal from the patient at one or more stages of a medical procedure at a flow rate greater than 60 L/min.

Clause 56. A method of increasing the pressure within a patient's airway, preventing the collapse of a patient's anatomy and/or clearing debris or smoke during one or more stages of the medical procedure using a high gas flow that is greater than 15 L/min.

Clause 57. A method of supporting respiratory function while a patient is under general anaesthesia and the patient is unconscious, comprising providing a high gas flow a high gas flow that is greater than 15 L/min during an apnoeic phase while the patient is under general anaesthesia and the patient is unconscious.

Clause 58. A method according to clause 57 wherein the high gas flow is greater than 30 L/min.

Clause 59. A method according to clause 57 wherein the high gas flow is greater than 70 L/min or greater than 80 L/min, or greater than 90 L/min, or greater than 100 L/min, or less than 150 L/min.

Clause 60. A method according to any of clauses 57 to 59 further comprising providing a high gas flow prior greater than 15 L/min prior the putting the patient under general anaesthesia.

Clause 61. A method according to clause 60 wherein the high gas flow prior to putting the patient under general anaesthesia is greater than 30 L/min, or greater than 40 L/min, or greater than 50 L/min, or greater than 60 L/min.

Clause 62. A method according to clause 61 wherein the high gas flow prior to putting the patient under general anaesthesia is greater than 70 L/min or greater than 80 L/min, or greater than 90 L/min, or up to 100 L/min.

Clause 63. A method according to any of clauses 57 to 62 comprising providing high gas flow greater than 15 L/min as the patient wakes from general anaesthesia.

Clause 64. A method according to any of clauses 57 to 63 comprising providing high gas flow greater than 30 L/min, or greater than 40 L/min, or greater than 50 L/min, or greater than 60 L/min, as the patient wakes from general anaesthesia.

Clause 65. A method according to any of clauses 57 to 64 comprising providing high gas flow greater than 70 L/min, or greater than 80 L/min, or greater than 90 L/min, or up to 100 L/min, as the patient wakes from general anaesthesia.

Clause 66. A high gas flow therapy apparatus for use in providing a high gas flow that is greater than 15 L/min during an apnoeic phase while the patient is under general anaesthesia and the patient is unconscious.

Clause 67. A method of providing ventilation while a patient is under general anaesthesia using only a gas flow delivered through a nasal interface while the patient is under general anaesthesia, the gas flow being greater than 15 L/min.

Clause 68. A method according to clause 67 wherein the gas flow is greater than or equal to 30 L/min.

Clause 69. A method according to clause 68 wherein the gas flow is greater than or equal to 70 L/min or greater than or equal to 80 L/min, or greater than or equal to 90 L/min, or greater than or equal to 100 L/min, or less than or equal to 150 L/min.

Clause 70. A method according to any of Clauses 67-69 wherein the patient is under general anaesthesia and unconscious.

It should be understood that any examples used in this description are in no way limiting, but merely illustrative of possible embodiments for purposes of clarification. Unless the context clearly requires otherwise, throughout this description and the claims that follow, the words "comprise", "comprising", and the like, are to be construed in an inclusive sense as opposed to an exclusive or exhaustive sense, that is to say, in the sense of "including, but not limited to".

Reference to any prior art in this description is not, and should not be taken as, an acknowledgement or any form of suggestion that the prior art referenced forms part of the common general knowledge in any relevant field of endeavour in any country in the world.

The present invention may be said broadly to consist in the parts, elements, and features referred to or indicated in this description and the claims that follow, individually or collectively, in any or all combinations of two or more of said parts, elements, or features. Where reference is made to integers or components having known equivalents thereof, those equivalents are herein incorporated as if individually set forth.

It should be noted that various modifications to the embodiments disclosed herein will be apparent to those skilled in the art. Such modifications may be made without departing from the spirit and scope of the present invention and without diminishing its attendant advantages. For instance, various components may be repositioned or reshaped as desired. It is therefore intended that such modifications be included within the scope of the invention. Moreover, not all of the features, aspects, and advantages disclosed herein are necessarily required to practice the present invention. Accordingly, the scope of the present invention is intended to be defined only by the claims that follow.

What is claimed:

1. A method for providing respiratory support to a patient during a medical procedure, the method comprising:
   providing a first flow rate of gas flow to a patient interface during the medical procedure; and
   providing a second flow rate of gas flow to the patient interface after the medical procedure,
   wherein the medical procedure is an anesthetic procedure, and
   wherein each of the first flow rate and the second flow rate is at least 15 L/min.

2. The method of claim 1, wherein the second flow rate of gas flow is provided to the patient interface during one or more of: a post-operative period, as the patient wakes from general anesthesia, or as the patient wakes from general anesthesia but while the patient is unconscious.

3. The method of claim 1, wherein the second flow rate is less than the first flow rate.

4. The method of claim 1, wherein the patient is spontaneously breathing.

5. The method of claim 1, wherein during the medical procedure the patient's respiration is depressed.

6. The method of claim 1, wherein the medical procedure comprises one or more of: a partial sedation or conscious sedation.

7. The method of claim 1, wherein the medical procedure is a general anesthesia procedure.

8. The method of claim 1, wherein the first flow rate of gas flow is provided during an apneic window.

9. The method of claim 1, wherein the patient interface comprises a non-sealing patient interface.

10. The method of claim 1, wherein the patient is administered anesthetic drugs at least one of: before or during the medical procedure.

11. The method of claim 1, further comprising providing a third flow rate of gas flow to the patient interface before the medical procedure.

12. The method of claim 11, wherein the third flow rate is less than the first flow rate.

13. The method of claim 12, wherein the third flow rate is at least 15 L/min.

14. The method of claim 12, wherein the third flow rate is at least 40 L/min.

15. The method of claim 11, wherein the second flow rate is equal to the third flow rate.

16. The method of claim 1, further comprising:
   determining whether the medical procedure has ended; and
   providing the second flow rate based on the determination.

17. The method of claim 1, wherein the second flow rate is gradually reduced.

18. The method of claim 1, wherein the second flow rate is the same as the first flow rate.

19. The method of claim 1, wherein the second flow rate is initially the same as the first flow rate and then is gradually reduced.

20. The method of claim 1, wherein the gas flow provided at the first flow rate comprises 100% oxygen.

21. The method of claim 1, wherein the gas flow provided at the second flow rate comprises less than 100% oxygen.

22. The method of claim 1, wherein each of the first flow rate and the second flow rate is at least 40 L/min.

23. The method of claim 1, wherein the first flow rate is at least 40 L/min.

24. The method of claim 1, wherein the first flow rate is at least 60 L/min.

25. The method of claim 1, wherein the second flow rate is at least 40 L/min.

26. The method of claim 1, wherein the first flow rate is between about 20 L/min to about 150 L/min and the second flow rate is between about 15 L/min to about 90 L/min.

27. The method of claim 1, further comprising humidifying the first flow rate of gas flow or the second flow rate of gas flow to contain greater than 10 mg/L of water.

28. A system comprising:
a patient interface;
a flow source; and
a controller configured to control the flow source to:
    provide a first flow rate of gas flow to the patient interface during a medical procedure, wherein the first flow rate is at least 15 L/min, and
    provide a second flow rate of gas flow to the patient interface after the medical procedure, wherein the second flow rate is at least 15 L/min,
    wherein the medical procedure is an anesthetic procedure.

29. The system of claim 28, wherein the first flow rate is between about 20 L/min to about 150 L/min and the second flow rate is between about 15 L/min to about 90 L/min.

30. The system of claim 28, further comprising a humidifier configured to humidify the first flow rate of gas flow or the second flow rate of gas flow to contain greater than 10 mg/L of water.

31. The system of claim 30, wherein the humidifier is configured to heat the first flow rate of gas flow or the second flow rate of gas flow to 21° C. to 42° C.

32. The system of claim 28, wherein the controller is configured to operate the flow source to provide the gas flow based on an output of one or more of a sensor or an input/output user interface.

33. The system of claim 32, wherein the flow source is configured to deliver the second flow rate of gas when the sensor determines the medical procedure has ended.

34. The system of claim 28, wherein each of the first flow rate and the second flow rate is at least 40 L/min.

35. The system of claim 28, wherein the first flow rate is at least 40 L/min.

36. The system of claim 28, wherein the first flow rate is at least 60 L/min.

37. The system of claim 28, wherein the second flow rate is at least 40 L/min.

38. The system of claim 28, wherein the second flow rate is less than the first flow rate.

39. The system of claim 28, wherein the controller is configured to control the flow source to provide a third flow rate of gas flow to the patient interface before the medical procedure.

40. The system of claim 39, wherein the third flow rate is less than the first flow rate.

41. The system of claim 39, wherein the second flow rate is equal to the third flow rate.

42. The system of claim 39, wherein the third flow rate is at least 15 L/min.

43. The system of claim 39, wherein the third flow rate is at least 40 L/min.

44. The system of claim 28, wherein the controller is configured to gradually reduce the second flow rate.

45. The system of claim 28, wherein the second flow rate is the same as the first flow rate.

46. The system of claim 28, wherein the second flow rate is initially the same as the first flow rate and then is gradually reduced.

47. The system of claim 28, wherein the gas flow provided at the first flow rate comprises 100% oxygen.

48. The system of claim 28, wherein the gas flow provided at the second flow rate comprises less than 100% oxygen.

49. A method for providing respiratory support to a patient during a medical procedure, the medical procedure comprising:
    providing a first flow rate of gas flow to a patient interface during the medical procedure;
    providing a second flow rate of gas flow to the patient interface after the medical procedure,
    wherein:
        the second flow rate is less than the first flow rate,
        each of the first flow rate and the second flow rate is at least 15 L/min,
        the gas flow is delivered to the patient via a non-sealing patient interface, and
        the medical procedure is an anesthetic procedure.

* * * * *